US007716066B2

(12) United States Patent
Rosow et al.

(10) Patent No.: US 7,716,066 B2
(45) Date of Patent: *May 11, 2010

(54) MANAGING PATIENT BED ASSIGNMENTS AND BED OCCUPANCY IN A HEALTH CARE FACILITY

(75) Inventors: Eric Rosow, Avon, CT (US); Joe Adam, West Hartford, CT (US); Chris Roth, West Hartford, CT (US)

(73) Assignee: Eclipsys Corporation, Irvine, CA (US)

( * ) Notice: Subject to any disclaimer, the term of this patent is extended or adjusted under 35 U.S.C. 154(b) by 164 days.

This patent is subject to a terminal disclaimer.

(21) Appl. No.: 11/841,345

(22) Filed: Aug. 20, 2007

(65) Prior Publication Data

US 2008/0065431 A1 Mar. 13, 2008
US 2008/0312972 A2 Dec. 18, 2008

Related U.S. Application Data

(63) Continuation of application No. 10/238,427, filed on Sep. 9, 2002.

(60) Provisional application No. 60/317,784, filed on Sep. 7, 2001.

(51) Int. Cl.
G06Q 10/00 (2006.01)
G06Q 50/00 (2006.01)

(52) U.S. Cl. ............... 705/2; 705/3; 705/4; 705/1; 340/5.53; 340/925.49; 600/300

(58) Field of Classification Search .......... 705/2–4; 340/5.54, 925; 600/300
See application file for complete search history.

(56) References Cited

U.S. PATENT DOCUMENTS

| 3,668,690 | A | 6/1972 | Ormond |
| 4,135,241 | A | 1/1979 | Stanis |
| 4,752,876 | A | 6/1988 | Couch et al. |
| 4,807,155 | A | 2/1989 | Cree et al. |
| 4,994,908 | A | 2/1991 | Kuban et al. |
| 5,065,315 | A | 11/1991 | Garcia |
| 5,331,549 | A | 7/1994 | Crawford, Jr. |
| 5,463,546 | A | 10/1995 | Parkhurst |
| 5,475,364 | A | 12/1995 | Kenet |

(Continued)

OTHER PUBLICATIONS

Information Disclosure Statement (IDS) Letter Regarding Common Patent Application(s), submitted by Applicant on Dec. 28, 2008.

*Primary Examiner*—Gerald J. O'Connor
*Assistant Examiner*—Linh-Giang Michelle Le
(74) *Attorney, Agent, or Firm*—Tillman Wright, PLLC; Chad D. Tillman; Jeremy C. Doerre

(57) ABSTRACT

An integrated health care delivery network with enabling software and network technology to maximize bed resources, manage varying census levels, and avoid patient diversions through real-time monitoring, automation and communication, is disclosed. Preferably, the present invention is embodied in a bed management system that interfaces with and complements existing Admission/Discharge/Transfer (ADT) systems. The bed management system is an easy-to-use business intelligence application that is designed to allow administrators, clinicians and managers to easily access, analyze and display real-time patient and bed availability information from ancillary information systems, databases and spreadsheets. It enables users to see trends and relationships in hospital (bed) management data directly from their desktop personal computers.

21 Claims, 42 Drawing Sheets

U.S. PATENT DOCUMENTS

| | | |
|---|---|---|
| 5,533,183 A | 7/1996 | Henderson, Jr. et al. |
| 5,581,461 A | 12/1996 | Coll et al. |
| 5,809,477 A | 9/1998 | Pollack |
| 5,823,948 A | 10/1998 | Ross et al. |
| 5,909,668 A | 6/1999 | Fukuma |
| 5,991,730 A | 11/1999 | Lubin et al. |
| 5,999,208 A | 12/1999 | McNerney et al. |
| 6,047,259 A | 4/2000 | Campbell et al. |
| 6,079,863 A | 6/2000 | Furukawa et al. |
| 6,101,534 A | 8/2000 | Rothschild |
| 6,163,903 A | 12/2000 | Weismiller |
| 6,356,874 B1 | 3/2002 | Ohrn |
| 6,362,725 B1 | 3/2002 | Ulrich et al. |
| 6,671,563 B1 | 12/2003 | Engelson et al. |
| 6,779,024 B2 | 8/2004 | DeLaHuerga |
| 6,897,780 B2 | 5/2005 | Ulrich et al. |
| 7,165,221 B2 | 1/2007 | Monteleone et al. |
| 7,287,290 B2 | 10/2007 | Romano et al. |
| 2001/0032195 A1* | 10/2001 | Graichen et al. ............ 705/400 |
| 2001/0050610 A1 | 12/2001 | Gelston |
| 2002/0013714 A1* | 1/2002 | Dubler et al. .................. 705/2 |
| 2002/0072911 A1* | 6/2002 | Kilgore et al. .............. 704/270 |
| 2002/0116219 A1 | 8/2002 | Ibok et al. |
| 2002/0158919 A1 | 10/2002 | Nacey |
| 2003/0050806 A1* | 3/2003 | Friesen et al. .................. 705/5 |
| 2003/0074222 A1 | 4/2003 | Rosow et al. |
| 2003/0078810 A1 | 4/2003 | Cole |
| 2003/0078811 A1 | 4/2003 | Cole |
| 2004/0243446 A1 | 12/2004 | Wyatt |
| 2005/0010441 A1 | 1/2005 | Wheeler |
| 2005/0219059 A1 | 10/2005 | Ulrich et al. |
| 2005/0283382 A1 | 12/2005 | Donoghue et al. |
| 2006/0004605 A1 | 1/2006 | Donoghue et al. |
| 2006/0114888 A1 | 6/2006 | Schuman |
| 2006/0143045 A1 | 6/2006 | Nacey |
| 2006/0247948 A1 | 11/2006 | Ellis et al. |
| 2007/0004971 A1 | 1/2007 | Riley et al. |
| 2007/0010719 A1 | 1/2007 | Huster et al. |
| 2007/0094045 A1 | 4/2007 | Cobbs |
| 2007/0094046 A1 | 4/2007 | Cobbs |
| 2007/0210917 A1 | 9/2007 | Collins, Jr. et al. |
| 2007/0247310 A1 | 10/2007 | Ulrich et al. |
| 2008/0065430 A1 | 3/2008 | Rosow et al. |
| 2008/0065432 A1 | 3/2008 | Rosow et al. |
| 2008/0065433 A1 | 3/2008 | Rosow et al. |
| 2008/0065434 A1 | 3/2008 | Rosow et al. |
| 2008/0221926 A1 | 9/2008 | Rosow et al. |
| 2009/0119127 A2 | 5/2009 | Rosow et al. |
| 2009/0254365 A1 | 10/2009 | Gravina |

* cited by examiner

| Segment | Sequence | Field Name |
|---|---|---|
| Message Header (MSH) | 4 | Sending Facility |
| MSH | 7 | Message Date & Time |
| MSH | 9.1 | Message Type ID |
| MSH | 9.2 | Trigger Event IDID |
| MSH | 10 | Message Control ID |
| MSH | 11 | Processing IDntrol ID |
| Patient Identification (PID) | 3.1 | Patient ID Internal ID |
| PID | 5.1 | Patient Last Name |
| PID | 5.2 | Patient First Name |
| PID | 5.3 | Patient Middle Name Initial |
| PID | 5.4 | Patient Suffix |
| PID | 5.5 | Patient Prefix |
| PID | 5.6 | Patient Degree |
| PID | 7 | Patient Date and Time of Birth |
| PID | 8 | Patient Sex |
| PID | 17 | Patient Religion |
| PID | 18.1 | Patient Account Number ID |
| PID | 19 | Patient Social Security Number |
| Patient Visit (PV1) | 2 | Patient Class |
| PV1 | 3.1 | Assigned Patient Location Nurse Unit |
| PV1 | 3.2 | Assigned Patient Location Room |
| PV1 | 3.3 | Assigned Patient Location Bed |
| PV1 | 3.4 | Assigned Patient Location Facility |
| PV1 | 3.5 | Assigned Patient Location Status |
| PV1 | 4 | Admission Type |
| PV1 | 7.1 | Attending Physician ID |
| PV1 | 7.2 | Attending Physician Last Name |
| PV1 | 7.3 | Attending Physician First Name |
| PV1 | 7.4 | Attending Physician Middle Name |
| PV1 | 7.5 | Attending Physician Suffix |
| PV1 | 7.6 | Attending Physician Prefix |
| PV1 | 7.7 | Attending Physician Degree |
| PV1 | 8.1 | Referring Physician ID |
| PV1 | 8.2 | Referring Physician Last Name |
| PV1 | 8.3 | Referring Physician First Name |
| PV1 | 8.4 | Referring Physician Middle Name |
| PV1 | 8.5 | Referring Physician Suffix |
| PV1 | 8.6 | Referring Physician Prefix |
| PV1 | 8.7 | Referring Physician Degree |
| PV1 | 10 | Hospital Service |
| PV1 | 14 | Admit Source |
| PV1 | 15 | Ambulatory Status |

FIG. 3

| Segment | Sequence | Field Name |
|---|---|---|
| PV1 | 16 | VIP Indicator |
| PV1 | 17.1 | Admitting Physician ID |
| PV1 | 17.2 | Admitting Physician Last Name |
| PV1 | 17.3 | Admitting PhysicianFirst Name |
| PV1 | 17.4 | Admitting PhysicianMiddle Name |
| PV1 | 17.5 | Admitting PhysicianSuffix |
| PV1 | 17.6 | Admitting PhysicianPrefix |
| PV1 | 17.7 | Admitting PhysicianDegree |
| PV1 | 18 | Patient Type |
| PV1 | 36 | Discharge Disposition |
| PV1 | 39 | Servicing Facility |
| PV1 | 44 | Admit Date and Time |
| PV1 | 45 | Discharge Date and Time |
| Patient Visit - Additional Information (PV2) | 8 | Expected Admit Date and Time |
| PV2 | 9 | Expected Discharge Date and Time |
| Merge Patient Information (MRG) | 1.1 | Prior Patient ID |
| Additional Clinical Data (ZCR) | 2 | Admit Symptoms |
| Custom Hartford Hospital Segment (Z01) | 7.1 | Place in Bed Date |
| Z01 | 7.2 | Place in Bed Time |
| Z01 | 7.3 | Release from Bed Date |
| Z01 | 7.4 | Release from Bed Time |

FIG. 4

BED Table:

| BED | PosPresIsol | Text(18) | NULL | Positive Pressure Isolation Required? |
|---|---|---|---|---|
| BED | LastUpdate | Dte/Time | NULL | Date and time of last update |
| BED | CreateDate | Date/Time | NULL | Date record created |
| BED | NearNurseStation | Yes/No | NULL | Near Nursing Station? |
| BED | Monitor | Yes/No | NULL | Patient Monitor? |
| BED | Overflow | Yes/No | NULL | Overflow bed |
| BED | SecurityPrecautions | Yes/No | NULL | Security available for this bed/location |
| BED | Sitter | Yes/no | NULL | Sitter available for this bed/location |
| BED | Name | Text(50) | NULL | Common name of bed |
| BED | NegPresIsol | Text(10) | NULL | Negative Pressure Isolation Required? |
| BED | BedID | Texct(10) | NULL | Unique bed identifier (PK) |
| BED | CreateUser | Text(50) | NULL | User that created record |
| BED | RoomID | Text(10) | NULL | Relationship to Room (FK) |
| BED | Status | Text(50) | NULL | Status of the bed |
| BED | UnitID | Text(10) | NULL | Unique ID |
| BED | Update User | Text(50) | NULL | User that last updated record |

FIG. 6A

MESSAGE TABLE:

| MESSAGE | MessageID | Integer | NOT NULL |
|---|---|---|---|
| MESSAGE | Message | Text(255) | NULL |

FIG. 6B

NOTES TABLE:

| NOTES | NotesID | Integer | NOT NULL |
|---|---|---|---|
| NOTES | Note | Memo | NULL |

FIG. 6C

PATIENT TABLE:

| | | | | |
|---|---|---|---|---|
| PATIENT | UpdateDate | Date/Time | NULL | Date and time record was last updated |
| PATIENT | PreAdmitDateBMD | Date/Time | NULL | |
| PATIENT | DischargeDate | Date/Time | NULL | Date & Time patient was discharged |
| PATIENT | DischargeDateADT | Date/Time | NULL | |
| PATIENT | DischargeDatekBMD | Date/Time | NULL | |
| PATIENT | PreAdmitDateADT | Date/Time | NULL | |
| PATIENT | PreAdmitDate | Date/Time | NULL | Date & Time patient was preadmitted (if appropriate) |
| PATIENT | DOB | Date/Time | NULL | Date of birth |
| PATIENT | AdmitDate | Date/Time | NULL | Date & Time patient was admitted |
| PATIENT | AdmitDateADT | Date/Time | NULL | |
| PATIENT | AdmitDateBMD | Date/Time | NULL | |
| PATIENT | SecurityPrecaution | Yes/No | NULL | Security required? |
| PATIENT | VRSA | Yes/No | NULL | VRSA? |
| PATIENT | AirbornIsol | Yes/No | NULL | Airborn Isolation Required? |
| PATIENT | SitterNeeded | Yes/No | NULL | Sitter required? |
| PATIENT | NotesID | Integer | NULL | |
| PATIENT | NegPresIsol | Yes/No | NULL | Negative Pressure Isolation Required? |
| PATIENT | MRSA | Yes/No | NULL | MRSA? |
| PATIENT | MonitorNeeded | Yes/No | NULL | |
| PATIENT | ContactIsol | Yes/No | NULL | Contact Isolation Required? |
| PATIENT | VRE | Yes/No | NULL | VRE? |
| PATIENT | PosPresIsol | Yes/No | NULL | Positive Pressure Isolation Required? |
| PATIENT | MessageID | Integer | NULL | |
| PATIENT | Pregnant | Yes/No | NULL | Patient Pregnant? |
| PATIENT | LengthOfStay | Single | NULL | Patient's Length Of Stay |
| PATIENT | PatientType | Text(10) | NULL | Patient Type (Inpatient or Outpatient) |
| PATIENT | AccountNumber | Text(50) | NULL | Hospital's account # for this patient visit |
| PATIENT | DischargeDisposition | Text(10) | NULL | Discharge Disposition (i.e., went home, skilled nursing facility, transferred to other facility, expired, etc.) |
| PATIENT | ADTService | Text(50) | NULL | Service as reported by ADT System |
| PATIENT | CurrentBedID | Text(10) | NULL | Unique ID for Bed for patient's current location (FK) |
| PATIENT | AdmittingDrNum | Text(10) | NULL | Admitting Physician ID Number |
| PATIENT | PatientID | Text(10) | NULL | Unique Patient ID for this application (PK) |
| PATIENT | LocAdmittedTo | Text(50) | NULL | Location that patient was admitted to |
| PATIENT | MedicalRecordNumber | Text(50) | NULL | Patient's Medical Record Number |

| | | | | |
|---|---|---|---|---|
| PATIENT | Gender | Text(50) | NULL | Gender (Sex) |
| PATIENT | FirstName | Text(50) | NULL | First Name |
| PATIENT | MiddleInitial | Text(50) | NULL | Middle Initial |
| PATIENT | AttendingDrName | Text(10) | NULL | |
| PATIENT | AmbulanceStatus | Text(10) | NULL | |
| PATIENT | PatientClass | Text(10) | NULL | |
| PATIENT | AttendingDrNum | Text(10) | NULL | |
| PATIENT | SocialSecurity | Text(10) | NULL | |
| PATIENT | PrimaryService | Text(50) | NULL | Primary Service |
| PATIENT | TriageLevel | Text(50) | NULL | Triage Level (Values from Lookup table) |
| PATIENT | AdmitSource | Text(50) | NULL | Location that patient was admitted via (PAT, ED, etc) |
| PATIENT | ServicingFacility | Text(50) | NULL | |
| PATIENT | AdmitSymptoms | Text(30) | NULL | |
| PATIENT | SecondaryService | Text(50) | NULL | Secondary Service |
| PATIENT | UnitID | Text(10) | NULL | If no bed is available, unit patient is assigned to. |
| PATIENT | AdmittingDrName | Text(10) | NULL | |
| PATIENT | VIPIndicator | Text(10) | NULL | |
| PATIENT | UpdateUser | Text(10) | NULL | User that last updated record |
| PATIENT | Religion | Text(10) | NULL | |
| PATIENT | ReferringDrNum | Text(10) | NULL | |
| PATIENT | ReferringDrName | Text(10) | NULL | |
| PATIENT | Status | Text(50) | NULL | Patient Status (Values from Lookup table) |
| PATIENT | LastName | Text(50) | NULL | Last Name |
| PATIENT | UnitDischargeFrom | Text(50) | NULL | Location that patient was discharged from |
| PATIENT | Admission Type | Text(10) | NULL | |

PATIENT_SCHEDULE TABLE:

| | | | | |
|---|---|---|---|---|
| PATIENT_SCHEDULE | Event | Text(8) | NULL | |
| PATIENT_SCHEDULE | ADTEnteredDate | Date/Time | NULL | SMS entered Date for this event |
| PATIENT_SCHEDULE | DateIn | Date/Time | NULL | Actual Date In for this event. |
| PATIENT_SCHEDULE | ExpectedDateTo | Date/Time | NULL | Expected Date finished at this event. |
| PATIENT_SCHEDULE | ExpectedDateFrom | Date/Tme | NOT NULL | Date this event is espected to begin. |
| PATIENT_SCHEDULE | DateOut | Date/Time | NULL | Actual Date Out for this event. |
| PATIENT_SCHEDULE | UnitID | Text(10) | NULL | Unit ID |
| PATIENT_SCHEDULE | Event | Text(18) | NULL | Event-- ADT_Assigned, BMD_Assigned, BMD_Requested, ADT_Temp, BMD_Temp, ADT_Discharged, BMD_Discharged. |
| PATIENT_SCHEDULE | BedID | Text(10) | NULL | BedID |
| PATIENT_SCHEDULE | PatientID | Text(10) | NOT NULL | Must have valid Patient ID from Patient Table. |

FIG. 6E

ROOM TABLE:

| | | | | |
|---|---|---|---|---|
| ROOM | LastUpdate | Date/Time | NULL | Date and time of last update |
| ROOM | CreateDate | Date/Time | NULL | Date record created |
| ROOM | Status | Text(18) | NULL | |
| ROOM | RoomID | Text(10) | NULL | Unique room identifier |
| ROOM | UpdateUser | Text(50) | NULL | User that last updated record |
| ROOM | Unit ID | Text(10) | NULL | Unique ID |
| ROOM | Name | Text(50) | NULL | Label commonly used to refer to this room |
| ROOM | CreateUser | Text(50) | NULL | User that created record |

FIG. 6F

UNIT TABLE:

| | | | | |
|---|---|---|---|---|
| UNIT | CreateDate | Date/Time | NULL | Date and time of record create |
| UNIT | UpdateDate | Date/Time | NULL | Date and time of last update |
| UNIT | MaxBeds | Long Integer | NULL | Maximum beds in unit |
| UNIT | Staffed Beds | Long Integer | NULL | Staffed beds (changed each shift) |
| UNIT | Status | Text(50) | NULL | From VL_Unit_Status |
| UNIT | Gender | Text(50) | NULL | Gender for this unit (M, F or A[ny]) |
| UNIT | CreateUser | Text(50) | NULL | User that created record |
| UNIT | Name | Text(50) | NULL | Common name of unit |
| UNIT | UnitID | Text(10) | NULL | Unique ID |
| UNIT | UpdateUser | Text(50) | NULL | User that modified record |

FIG. 6G

UNIT SERVICE TABLE:

| UNIT SERVICE | ServiceID | Text(10) | NULL |
|---|---|---|---|
| UNIT SERVICE | UnitID | Text(10) | NULL |

FIG. 6H

MISC. TABLES:

| VL_BED_STATUS | Status | Text(18) | NULL | |
|---|---|---|---|---|
| VL_PATIENT_STATUS | Status | Text(18) | NULL | |
| VL_PS_EVENT | Event | Text(18) | NOT NULL | |
| VL_ROOM_STATUS | Status | Text(18) | NULL | |
| VL_SERVICE | ServiceID | Text(10) | NULL | Service ID |
| VL_SERVICE | Name | Text(50) | NULL | Service Name |
| VL_U_STATUS | Status | Text(18) | NULL | |

FIG. 6I xATTRIBUTE TABLE:

| xAttribute | Last_update | Date/Time | NULL | Date and time of last update |
|---|---|---|---|---|
| xAttribute | Attribute_read_leve | Byte | NULL | Read user access level (0=all) |
| xAttribute | Numeric_default | Long Integer | NULL | Default value for attributes of num_range type |
| xAttribute | Numeric_high | Long Integer | NULL | Highest valid value for attributes of num_range type |
| xAttribute | Numeric_low | Long Integer | NULL | Lowest valid value for attributes of num_range type |
| xAttribute | Attribute_write_level | Byte | NULL | Write/Change user access level (0=all) |
| xAttribute | Notes | Text(50) | NULL | Free text to describe attribute, if necessary |
| xAttribute | Assessment_logic | Text(50) | NULL | Logic identifier to be used when determining patient assignment to beds (Nearest, Highest, Equal, Active, etc) |
| xAttribute | Attribute_label | Text(50) | NULL | Description of attribute |
| xAttribute | Unit_summary_method | Text(50) | NULL | Method identifier to be used when summarizing attribute at the Unit level (Average, Count_non_zero, etc) |
| xAttribute | Attribute_type | Text(50) | NULL | num_range or alpha_list |
| xAttribute | Attribute_required | Text(50) | NULL | Attribute tables that require this attribute (U,R,B,P - concatenated) |

FIG. 6J xATTRIBUTE VALUE TABLE:

| xAttribute Value | Last_update | Date/Time | NULL | Date and time of last update |
|---|---|---|---|---|
| xAttribute Value | System_Primary_Key | AutoNumber | NULL | |
| xAttribute Value | Attribute_value_write_level | Byte | NULL | User access level required to assign an attribute this value |
| xAttribute Value | Attribute_default_value_usage | Text(50) | NULL | Tables where this attribute value is to be used as a default |
| xAttribute Value | Attribute_label | Text(50) | NULL | Description of this attribute |
| xAttribute Value | Attribute_value_usage | Text(50) | NULL | Tables where this attribute value is valid |
| xAttribute Value | Attribute_value | Text(50) | NULL | Value of this attribute |

FIG. 6K yBED ATTRIBUTE TABLE:

| yBed Attribute | Last_update | Date/Time | NULL | Date and time of last update |
|---|---|---|---|---|
| yBed Attribute | System_Primary_Key | AutoNumber | NULL | |
| yBed Attribute | Attribute_Label | Text(50) | NULL | Name of attribute |
| yBed Attribute | Bed_ID | Text(50) | NULL | Unique identifier |
| yBed Attribute | Attribute_used_as_value | Text(50) | NULL | Value based on actual inherited usage |
| yBed Attribute | Attribute_intrinsic_value | Text(50) | NULL | Value assigned |

FIG. 6L yEVENT TABLE:

| yEvent | System_DT | Date/Time | NULL | Date and time stamp via system clock |
|---|---|---|---|---|
| yEvent | Message_DT | Date/Time | NULL | Date and time stamp via via message (if appropriate) |
| yEvent | System_Primary_Key | AutoNumber | NULL | |
| yEvent | Encrypted_User_ID | Text(50) | NULL | Encrypted User ID |
| yEvent | Attribute_label | Text(50) | NULL | Attribute affected (if appropriate) |
| yEvent | Event | Text(50) | NULL | System event code |
| yEvent | Location_ID | Text(50) | NULL | Unique identifier of unit, room or bed (if appropriate) |
| yEvent | Patient_ID | Text(50) | NULL | Unique patient ID (if appropriate) |
| yEvent | Event_data | Text(50) | NULL | Data value associated with this event |

FIG. 6M yPATIENT ATTRIBUTE TABLE:

| yPatient Attribute | Last_update | Date/Time | NULL | Date and time of last update |
|---|---|---|---|---|
| yPatient Attribute | Attribute_priority | Byte | NULL | 0=ignore,1=low,2=medium,3=high |
| yPatient Attribute | System_Primary_Key | AutoNumber | NULL | |
| yPatient Attribute | Attribute_label | Text(50) | NULL | Name of attribute |
| yPatient Attribute | Patient_ID | Text(50) | NULL | Unique ID |
| yPatient Attribute | Attribute_value | Text(50) | NULL | Value assigned to attribute |

FIG. 6N yROOM ATTRIBUTE TABLE:

| | | | | |
|---|---|---|---|---|
| yRoom Attribute | Last_update | Date/Time | NULL | Date and time of last update |
| yRoom Attribute | Attribute_summary_value | Single | NULL | Numeric value for roll-up summaries |
| yRoom Attribute | System_Primary_Key | AutoNumber | NULL | |
| yRoom Attribute | Room_ID | Text(50) | NULL | Unique identifier |
| yRoom Attribute | Attribute_Label | Text(50) | NULL | Name of attribute |
| yRoom Attribute | Attribute_used_as_value | Text(50) | NULL | Value based on actual inherited usage |
| yRoom Attribute | Attribute_intrinsic_value | Text(50) | NULL | Value assigned |

FIG. 6O yUNIT ATTRIBUTE TABLE:

| | | | | |
|---|---|---|---|---|
| yUnit Attribute | Last_update | Date/Time | NULL | Date and time of last update |
| yUnit Attribute | Attribute_summary_value | Single | NULL | Numeric value for roll-up summaries |
| yUnit Attribute | System_Primary_Key | AutoNumber | NULL | |
| yUnit Attribute | Unit_ID | Text(50) | NULL | Unique identifier |
| yUnit Attribute | Attribute_Label | Text(50) | NULL | Name of attribute |
| yUnit Attribute | Attribute_used_as_value | Text(50) | NULL | Value based on actual inherited usage |
| yUnit Attribute | Attribute_intrinsic_value | Text(50) | NULL | Value assigned |

FIG. 6P zARCHIVED BED CONFIGS TABLE:

| | | | | |
|---|---|---|---|---|
| zArchived Bed Configs | First_valid_DT | Date/Time | NULL | First time that this config is valid |
| zArchived Bed Configs | Last_valid_DT | Date/Time | NULL | Last time that this config is valid |
| zArchived Bed Configs | System_Primary_Key | AutoNumber | NULL | |
| zArchived Bed Configs | Bed_ID | Text(50) | NULL | Unique bed identifier |
| zArchived Bed Configs | Unit_ID | Text(50) | NULL | Unique unit identifier |
| zArchived Bed Configs | Bed_label | Text(50) | NULL | Common name of bed |
| zArchived Bed Configs | Room_ID | Text(50) | NULL | Unique room identifier |

FIG. 6Q zARCHIVED EVENTS TABLE:

| | | | | |
|---|---|---|---|---|
| zArchived Events | Message_DT | Date/Time | NULL | Date and time stamp via message (if appropriate) |
| zArchived Events | System_Primary_Key | Date/Time | NULL | |
| zArchived Events | Encrypted_User_ID | Text(50) | NULL | Encrypted User ID |
| zArchived Events | Location_ID | Text(50) | NULL | Unique identifier of unit, room or bed (if appropriate) |
| zArchived Events | Event | Text(50) | NULL | System event code |
| zArchived Events | Event_data | Text(50) | NULL | Data value associated with this event |
| zArchived Events | Attribute_label | Text(50) | NULL | Attribute affected (if appropriate) |
| zArchived Events | Patient_ID | Text(50) | NULL | Unique patient ID (if appropriate) |

FIG. 6R zARCHIVED PATIENT ATTRIBUTES TABLE:

| zArchived Patient Attributes | Last_update | Date/Time | NULL | Date and time of last update |
|---|---|---|---|---|
| zArchived Patient Attributes | Attribute_priority | Byte | NULL | 0=ignore,1=low,2=medium,3=high |
| zArchived Patient Attributes | System_Primary_Key | AutoNumber | NULL | |
| zArchived Patient Attributes | Patient_ID | Text(50) | NULL | Unique ID |
| zArchived Patient Attributes | Attribute_value | Text(50) | NULL | Value assigned to attribute |
| zArchived Patient Attributes | Attribute_label | Text(50) | NULL | Name of attribute |

FIG. 6S zARCHIVED PATIENTS TABLE:

| zArchived Patients | Patient_DOB | Date/Time | NULL | Date of birth |
|---|---|---|---|---|
| zArchived Patients | Patient_discharge_DT | Date/Time | NULL | Date & Time patient was discharged |
| zArchived Patients | Patient_bed_assigned_DT | Date/Time | NULL | Date & Time patient was assigned to a bed |
| zArchived Patients | Patient_admit_DT | Date/Time | NULL | Date & Time patient was admitted |
| zArchived Patients | Last_update | Date/Time | NULL | Date and time of last update |
| zArchived Patients | Patient_preadmit_DT | Date/Time | NULL | Date & Time patient was preadmitted (if appropriate) |
| zArchived Patients | System_Primary_Key | AutoNumber | NULL | |
| zArchived Patients | Patient_qty_units | Long Integer | NULL | Number of units this patient was assigned to during this stay |
| zArchived Patients | Patient_LOS | Single | NULL | Patient's Length Of Stay |
| zArchived Patients | Patient_ID | Text(50) | NULL | Unique Patient ID for this application |
| zArchived Patients | Patient_Medical_Record_Number | Text(50) | NULL | Patient's Medical Record number |
| zArchived Patients | Patient_Account_Number | Text(50) | NULL | Hospital's account # for this patient visit |
| zArchived Patients | Patient_admitted_to | Text(50) | NULL | Location that patient was admitted to |
| zArchived Patients | Patient_admitted_via | Text(50) | NULL | Location that patient was admitted via (PAT, ED, etc.) |
| zArchived Patients | Patient_discharged_from | Text(50) | NULL | Location that patient was discharged from |
| zArchived Patients | Patient_mi | Text(50) | NULL | Middle Initial |
| zArchived Patients | Patient_fname | Text(50) | NULL | First Name |
| zArchived Patients | Patient_lname | Text(50) | NULL | Last Name |

FIG. 6T zARCHIVED ROOM CONFIGS TABLE:

| | | | | |
|---|---|---|---|---|
| zArchived Room Configs | First_valid_DT | Date/Time | NULL | First time that this config is valid |
| zArchived Room Configs | Last_valid_DT | Date/Time | NULL | Last time that this config is valid |
| zArchived Room Configs | System_Primary_Key | AutoNumber | NULL | |
| zArchived Room Configs | Room Label | Text(50) | NULL | Label commonly used to refer to this room |
| zArchived Room Configs | Room ID | Text(50) | NULL | Unique room identifier |
| zArchived Room Configs | Unit ID | Text(50) | NULL | Unique unit identifier |

FIG. 6U zARCHIVED UNIT ATTRIBUTED TABLE:

| | | | | |
|---|---|---|---|---|
| zArchived Unit Attributes | Last_update | Date/Time | NULL | Date and time of last update |
| zArchived Unit Attributes | Attribute_summary_value | Single | NULL | Numeric value for roll-up summaries |
| zArchived Unit Attributes | System_Primary_Key | AutoNumber | NULL | |
| zArchived Unit Attributes | Unit_ID | Text(50) | NULL | Unique identifier |
| zArchived Unit Attributes | Attribute_intrinsic_value | Text(50) | NULL | Value assigned |
| zArchived Unit Attributes | Attribute_used_as_value | Text(50) | NULL | Value based on actual inherited usage |
| zArchived Unit Attributes | Attribute_label | Text(50) | NULL | Name of attribute |

FIG. 6V zARCHIVED ROOM CONFIGS TABLE:

| | | | | |
|---|---|---|---|---|
| zArchived Unit Configs | First_valid_DT | Date/Time | NULL | First time that this config is valid |
| zArchived Unit Configs | Last_valid_DT | Date/Time | NULL | Last time that this config is valid |
| zArchived Unit Configs | System_Primary_Key | AutoNumber | NULL | |
| zArchived Unit Configs | Unit_Label | Text(50) | NULL | |
| zArchived Unit Configs | Unit ID | Text(50) | NULL | Unique unit identifier |

FIG. 6W zUNIT SECURITY TABLE:

| | | | | |
|---|---|---|---|---|
| zUnit Security | System_Primary_Key | AutoNumber | NULL | |
| zUnit Security | Unit_Write_Level | Byte | NULL | Write access level for this User and Unit |
| zUnit Security | Unit_Read_Level | Byte | NULL | Read access level for this User and Unit |
| zUnit Security | Encrypted_User_ID | Text(50) | NULL | Encrypted User ID |
| zUnit Security | Encrypted_Unit_ID | Text(50) | NULL | Encrypted Unique Unit ID |
| zUnit Security | User_System_Security_Level | Byte | NULL | System Security Access Level for this user |
| zUnit Security | User_Initial_View | Text(50) | NULL | ID of initial view at login |
| zUnit Security | Encrypted_User_Password | Text(50) | NULL | Encrypted User Password |
| zUnit Security | Encrypted_User_ID | Text(50) | NULL | Encrypted User ID |
| zUnit Security | User_Initial_Unit | Text(50) | NULL | Default Unique unit ID at login |

FIG. 6X

PATIENT_STAY TABLE:

| Field Name | Data Source | Field Name | Data Source |
|---|---|---|---|
| PatientStayID | Internal Generated Unipue ID | ReferringDrNum | ADT |
| SocialSecurity | ADT | ReferringDrName | ADT |
| AccountNumber | ADT | AdmittingDrNum | ADT |
| MedicalRecordNumber | ADT | AdmittingDrName | ADT |
| LastName | ADT | AttendingDrNum | ADT |
| FirstName | ADT | AttendingDrName | ADT |
| MiddleName | ADT | DischargeDate | ADT |
| DOB | ADT | UnitDischargeFrom | ADT |
| Age | Internally generated from DOB | LengthOfstay | ADT |
| Religion | ADT | PreAdmitDateADT | ADT |
| Gender | ADT | PreAdmitDateBMD | ADT Interface |
| ADTService | ADT | BMDReqAdmitDate | BMD |
| BMDPrimaryService | BMD | AdmitDateADT | ADT |
| BMDSecondaryService | BMD | AdmitDateBMD | ADT Interface |
| ADTPatientClass | ADT | DischargeDateADT | ADT |
| BMDPatientClass | BMD | DischargeDateBMD | ADT Interface |
| ADTPatientType | ADT | DischargeDisposition | ADT |
| BMDPatientType | BMD | ServicingFacility | ADT |
| VIPIndicator | ADT | AmbulatoryStatus | ADT |
| Status | Generated by ADT Interface | PatientNoteID | BME |
| BMDStatus | BMD | DiagNoteID | BME |
| TriageLevel | BMD | PlaceInBedDate | ADT |
| SitterNeeded | BMD | ReleaseFromBedDate | ADT |
| SecurityPrecautionNeeded | BMD | PatientLocation | ADT |
| NearNurseStationNeeded | BMD | CurrentUnit | ADT |
| NegPresIsolNeeded | BMD | PendingDischargeDate | ADT |
| PosPresIsolNeeded | BMD | CreateUser | ADT Interface or BMD |
| ContactIsolNeeded | BMD | CreateDate | Internally Generate |
| BedsideMonitorNeeded | BMD | UpdateUser | ADT Interface or BMD |
| TelemetryMonitorNeeded | BMD | UpdateDate | Internally Generated |
| TelemetryMonitorUsed | BMD | UserLock | BMD |
| AirbornIsolNeeded | BMD | | |
| VRSA | BMD | | |
| VRE | BMD | | |
| MRSA | BMD | | |
| NeutropenicImmunosupressed | BMD | | |
| TBPCRRuleOutOrPos | BMD | | |
| TraumaMultitrauma | BMD | | |
| Pregnant | ADT | | |
| AdmitSymptoms | ADT | | |
| PreAdmitDate | ADT | | |
| AdmissionType | ADT | | |
| AdmitDate | ADT | | |
| AdmitSource | ADT | | |
| UnitAdmittedTo | ADT | | |
| BMDDateofArrival | BMD | | |
| BMDAdmitSourceType | BMD | | |
| BMDAdmitSourceName | BMD | | |
| BMDAdmitSourcePhone | BMD | | |
| BMDInputToInpt | BMD | | |
| BMDMedicaid | BMD | | |
| BMDCNCURNumber | BMD | | |
| BMDAdmitNoteID | BMD | | |
| BMDAdmitDiagnosis | BMD | | |
| BMDAdmitDrName | BMD | | |
| BMDDiagnosis | BMD | | |
| BMDVitalSigns | BMD | | |
| BMDLabValues | BMD | | |
| BMDAdmitType | BMD | | |
| BMDLevelofCare | BMD | | |
| BMDFellowResident | BMD | | |
| BMDAttendingDrName | BMD | | |
| BMDOnOffService | BMD | | |

FIG. 6Y

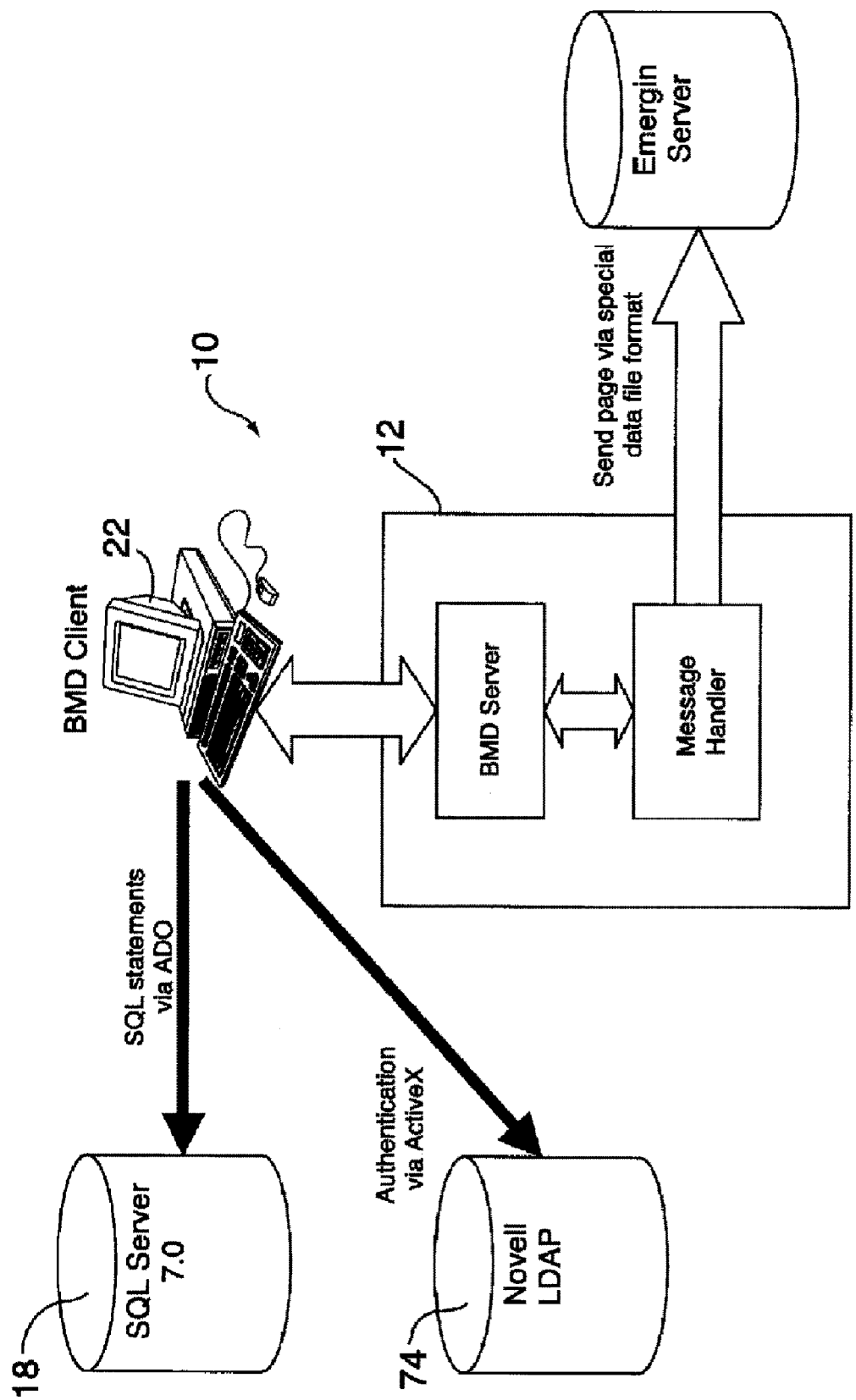

| | A | B | C | D | E | F | G | H | I | J | K | L | M | N | O | P | Q | R | S | T | U | V |
|---|---|---|---|---|---|---|---|---|---|---|---|---|---|---|---|---|---|---|---|---|---|---|
| 1 | | | Occ Now 416 | | | | Avail Now 335 | | | Total Cap 751 | | | | | | | | | | | PIT 9/5/02 1:41 AM | |
| 2 | | | Occ PIT 416 | | | | Avail PIT 335 | | | | | | | | | | | | | | | |
| 3 | | | | | | | | | | | | | | | | | | | | | | |
| 4 | Unit | Phone | Department | Max | Avail | Occ | Occ PIT | Resource | AM | D/C | M | F | Mx P | NC | P1 | PO | Mn | NP | PP | Comments | | Added |
| 5 | B11I | 55176 | medicine | 12 | 12 | 10 | 10 | | | | | | | 2 | | | | | | | | |
| 6 | B10I | 55400 | cardiology | 12 | 12 | 8 | 8 | | | | | | | 4 | | | | | | | | |
| 7 | B9I | 55200 | cardiothoracic | 12 | 12 | 2 | 2 | | | | | | | 10 | | 1 | | | | | | |
| 8 | C9WI | 51425 | neuro/trauma | 10 | 10 | 2 | 2 | | | | | | | 8 | | | | | | | | |
| 9 | B7I | 55100 | general surgery | 12 | 12 | 8 | 8 | | | | | | | 4 | | | | | | | | |
| 10 | B11S | 55165 | medicine | 3 | 3 | 3 | 3 | | | | | | | | | 1 | | | | | | |
| 11 | C9EI | 50123 | cardio/surg | 8 | 8 | 3 | 1 | | | | | | | 7 | | 1 | | | | | | |
| 12 | B7S | 55150 | general surgery | 3 | 3 | 3 | 1 | | | | | | | 2 | | | | | | | | |
| 13 | B9S | 55299 | cardio/surg | 3 | 3 | 2 | 2 | | | | | | 1 | | | | | | | | | |
| 14 | B11E | 55133 | med/pulmonary | 24 | 24 | 19 | 19 | | | | 3 | 2 | | 2 | 4 | | 5 | 11 | | | | |
| 15 | N12 | 51830 | med/GI dialysis | 26 | 26 | 10 | 10 | | | | 4 | | | 1 | | 1 | | | 2 | | | |
| 16 | C12 | 51833 | medicine/HIV | 12 | 12 | 22 | 22 | | | | 2 | 1 | | 2 | 10 | | | | | | | |
| 17 | CB5 | 51733 | med/oncology | 26 | 26 | 19 | 19 | | | | 1 | 2 | | 1 | 2 | | | | | | | |
| 18 | B5E | 50250 | med/surg/flex | 42 | 42 | 40 | 40 | | | | | | | 1 | | | | 12 | | | | |
| 19 | B10E | 55499 | cardio/dysrthyth | 28 | 23 | 23 | 23 | | | | 2 | 1 | | 2 | 2 | 6 | 9 | 23 | | | | |
| 20 | N10 | 51630 | plasty/chest pain | 26 | 26 | 15 | 15 | | | | 1 | 2 | | 2 | 6 | 1 | | 14 | | | | |
| 21 | C10 | 51633 | cardiology/CHF | 26 | 26 | 10 | 10 | | | | 1 | 2 | | 2 | 12 | 1 | | 19 | 1 | | | |
| 22 | N11 | 52272 | transplant | 26 | 26 | 12 | 12 | | | | 1 | 3 | | 2 | 8 | | | 6 | 1 | | | |
| 23 | N9 | 51430 | neuro/trauma/ent | 34 | 34 | 22 | 22 | | | | 2 | 4 | | 2 | 4 | 2 | | 17 | | | | |
| 24 | B9E | 55299 | cardio/surg | 24 | 24 | 22 | 22 | | | | 1 | 1 | | | | | 3 | 6 | | | | |
| 25 | B8 | 55906 | gen surg/urology | 42 | 42 | 28 | 28 | | | | 2 | | | 12 | | | | -1 | | | | |
| 26 | B7E | 55199 | vasc thoracic | 24 | 24 | 22 | 22 | | | | 1 | 1 | | | | | | | | | | |
| 27 | CB6 | 52170 | ortho/OMF | 42 | 42 | 13 | 13 | | | | 3 | 5 | | 5 | 16 | 1 | 2 | | | | | |
| 28 | CB5R | 54399 | rehab | 20 | 20 | 2 | 2 | | | | | 1 | | 7 | 10 | | | | | | | |
| 29 | CB4 | 50430 | hosp/pal care/DNR | 15 | 15 | 11 | 11 | | | | | | | | 4 | | | | | | | |
| 30 | N8 | 51330 | gyn/anti-partum | 32 | 32 | 24 | 24 | | | | 3 | | | 1 | 4 | | | | | | | |
| 31 | B6M | 52167 | obj/post-partum | 38 | 38 | 9 | 9 | | | | | | | 29 | | | | | | | | |
| 32 | D1N | ph:1234 | D1NText | 30 | 30 | 5 | 5 | | | | 1 | | | 2 | 22 | | | | | | | |

FIG. 29

MANAGING PATIENT BED ASSIGNMENTS AND BED OCCUPANCY IN A HEALTH CARE FACILITY

CROSS REFERENCE TO RELATED APPLICATIONS

The present application is a U.S. continuation patent application of, and claims priority under 35 U.S.C. §120 to, U.S. nonprovisional patent application Ser. No. 10/238,427, filed Sep. 9, 2002, which '427 application is incorporated by reference herein and which '427 application is a nonprovisional patent application of, and claims priority under 35 U.S.C. §119(e) to, U.S. provisional patent application Ser. No. 60/317,784, filed on Sep. 7, 2001, which '784 application is incorporated by reference herein.

The present application further incorporates by reference U.S. patent application publication no. US/2008/0221926, which is the publication of U.S. nonprovisional patent application Ser. No. 12/119,664, filed May 13, 2008. The '664 application represents the filing of the incorporated '784 provisional application as a nonprovisional application.

The present invention generally relates to the fields of automated resource management and virtual instrument technology. More particularly, the present invention relates to a real-time support tool for patient bed assignments and other process in a health care facility and for profiling historical, current and future activities and events such as bed occupancy levels therein.

BACKGROUND OF INVENTION

Most hospitals employ an Admission/Discharge/Transfer (ADT) system for managing ancillary information, such as admissions, discharge and transfer data about its patients. However, there are existing problems in ADT systems. One problem, for example, is the inability of current ADT systems to provide sufficient clinical information for appropriate patient placement.

Another problem area is the lack of accurate bed availability information. This generally results in lost admissions and excessive wait times.

Inefficient communication while searching for the appropriate bed for a patient, is another problem.

High incidences of 'observation' outpatients that occupy inpatient beds without payer authorization, is another problem.

Additionally, current ADT systems often lack the ability to access and provide meaningful historical, current and predictive data regarding bed occupancy levels and other activities and events related to the operation of a health care facility.

SUMMARY OF INVENTION

The present invention satisfies, to a great extent, the foregoing and other needs not currently satisfied by existing systems. This result is achieved, in an exemplary embodiment, by providing an integrated health care delivery network with enabling technology to maximize bed resources, manage varying census levels, and avoid patient diversions through real-time monitoring, automation and communication.

Preferably, the present invention is embodied in a bed management system that interfaces with and complements existing health care facilities admission systems such as Admission/Discharge/Transfer (ADT) systems. The bed management system is an easy-to-use intelligent application that is designed to allow administrators, clinicians and managers to easily access, analyze and display real-time patient and bed availability and related information from ancillary information systems, databases and spreadsheets. In other words, it enables users to see trends and relationships in hospital management data directly from their desktop personal computers and/or handheld personal digital assistants (PDAs).

The present invention improves patient placement efficiency and saves time and money by assisting with the clinical and business decision process that occurs when a patient needs to be admitted to a hospital, for instance. The system includes the use of virtual instruments to provide a cross-functional view of enterprise status throughout a facility or organization. Decision makers can easily move from big-picture analyses to transaction-level details while, at the same time, safely sharing this information throughout the enterprise to derive knowledge and make timely, data-driven decisions.

The system of the present invention enables more efficient patient placement by, for example, reducing/eliminating telephone calls and paper processes, and automatically matching patient requirements to available resources. In addition, it is an extremely powerful data warehouse and data mining tool that provides on-demand historical, real-time and predictive reports, alerts and recommendations.

The system of the present invention is real-time and mission critical. That is, it handles both scheduled and emergency events. The system also assists with the clinical and business decision processes that occur when a patient needs to be assigned to a specific bed location, for example.

Collectively, the system provides organizations or enterprises with an array of enabling technologies to: schedule/reserve/request patient bed assignments; assign/transfer patients from an emergency department and/or other clinical areas; reduce/eliminate dependency on telephone calls to communicate patient and bed requirements; apply statistical process control (SPC) and "Six Sigma" methodologies to manage occupancy and patient diversion; and provide administrators, managers and caregivers with accurate and on-demand reports and automatic alerts such as through pagers, electronic mail, telephone and intelligent software agents.

Other features of the present invention include: easy-to-use visual navigation; intuitive interactive interface; easy queries; runs on standard computers; real-time, historical and predictive analyses; user configurable settings; remote access and control; geographical information system interfaces; text-to-speech conversion; interactive agent support and alarms; automatic messaging via email, pagers, telephone, etc.; integrated online help; file management and configuration utilities. In addition to these features, the present invention bed management system is designed to protect patient confidentiality and be fully compliant with the evolving Health Insurance Portability and Accountability Act (HIPAA) regulations. A full security system is embedded within the dashboard to authenticate users, audit user access and assign users to definable system roles. These roles restrict both processes and the ability to view or change key data.

With these and other advantages and features of the invention that may become hereinafter apparent, the nature of the invention may be more clearly understood by reference to the following detailed description of the invention and to the several drawings attached herein.

BRIEF DESCRIPTION OF PREFERRED EMBODIMENTS

FIGS. 3 and 4 are tables illustrating patient data extracted from an HL7 message received from the ADT system of a health care facility.

FIGS. 6A-6Y are illustrations of the data tables and fields thereof as stored in the database of FIG. 5.

FIG. 7 is a diagram of the system of the present invention coupled to an authentication module for the network of the health care facility.

FIG. 12 is one embodiment of a user screen generated by the system for entering a patient into the bed management system.

FIG. 13 is another embodiment of the user screen of FIG. 12 used for locating a patient.

FIG. 14 is one embodiment of a user screen for entering patient details into the bed management system.

FIG. 15 is one embodiment of a find bed user screen of the system for identifying an appropriate bed for a selected patient; the beds in the facility sorted by clinical units.

FIG. 16 is one embodiment of a find bed user screen of the system for locating a bed for a selected patient, wherein any patient required bed attributes are entered into the bed management system.

FIG. 17 is one embodiment of a bed details user screen of the system for entering bed attributes for a particular bed into the system of the invention.

FIG. 18 is one embodiment of a placement information and confirmation user screen of the bed management system.

FIGS. 22 and 23 illustrate user interface screens of the present invention for accessing unit details in that table views.

FIG. 27 is one embodiment of a user interface screen of the present invention for matching the records of the bed management system of the invention with the records of the health care facility coupled thereto.

FIG. 28 is one embodiment of a census report generated by the system for accessing performance and census data for the clinical units, service groups and physicians of a health care facility.

FIG. 29 is one embodiment of an administrators report summarizing the bed occupancy and census data of a health care facility.

Figure 33:
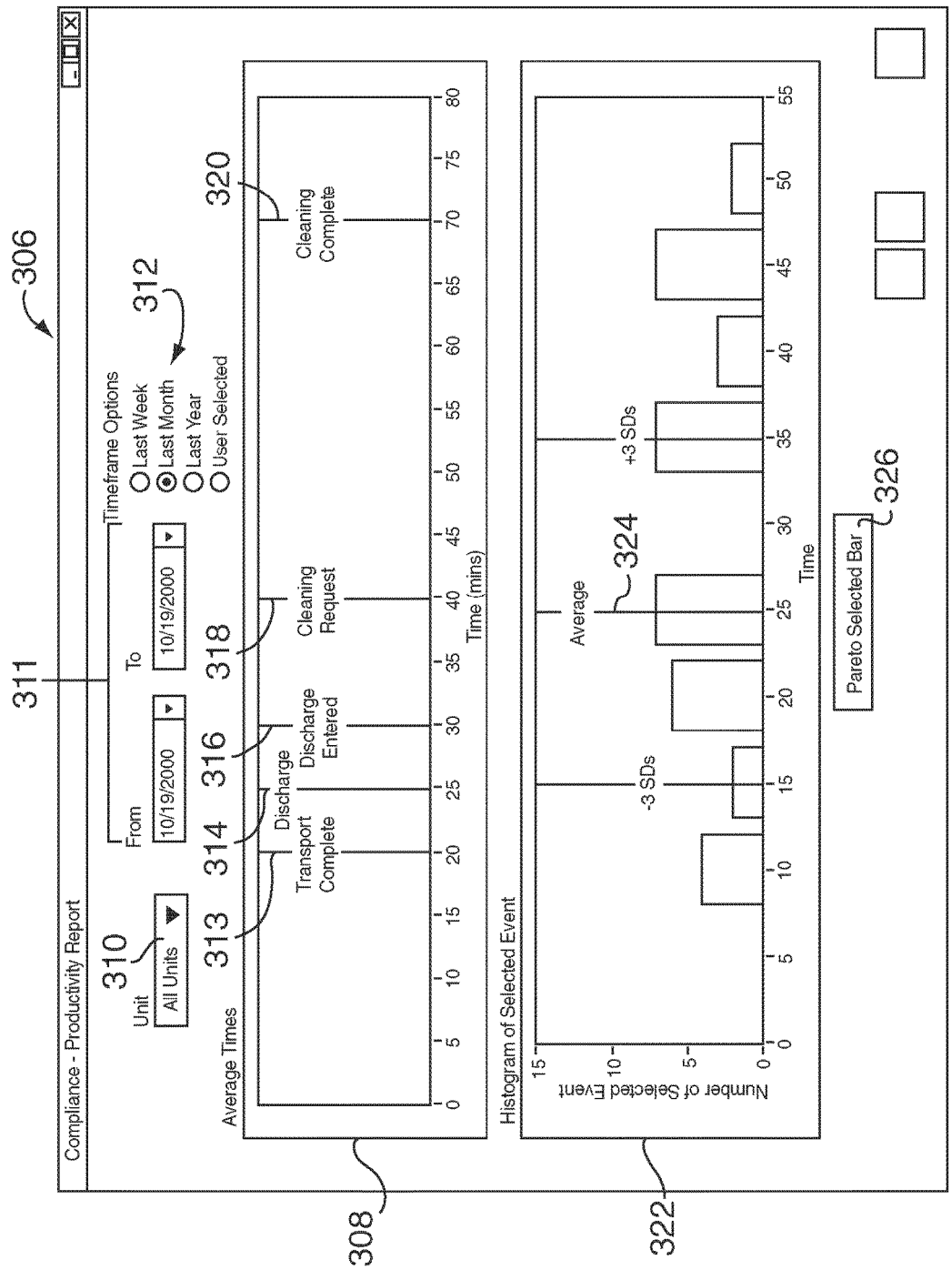

FIG. 33 is one embodiment of a productivity report generated by the bed management system of the present invention showing an average times for a discharge transaction and room cleaning operation to be completed for all units of a health care facility. A lower portion of the report shows one embodiment of a standard deviation chart for the selected activity of cleaning a bed in all units of the health care facility.

Figure 34:
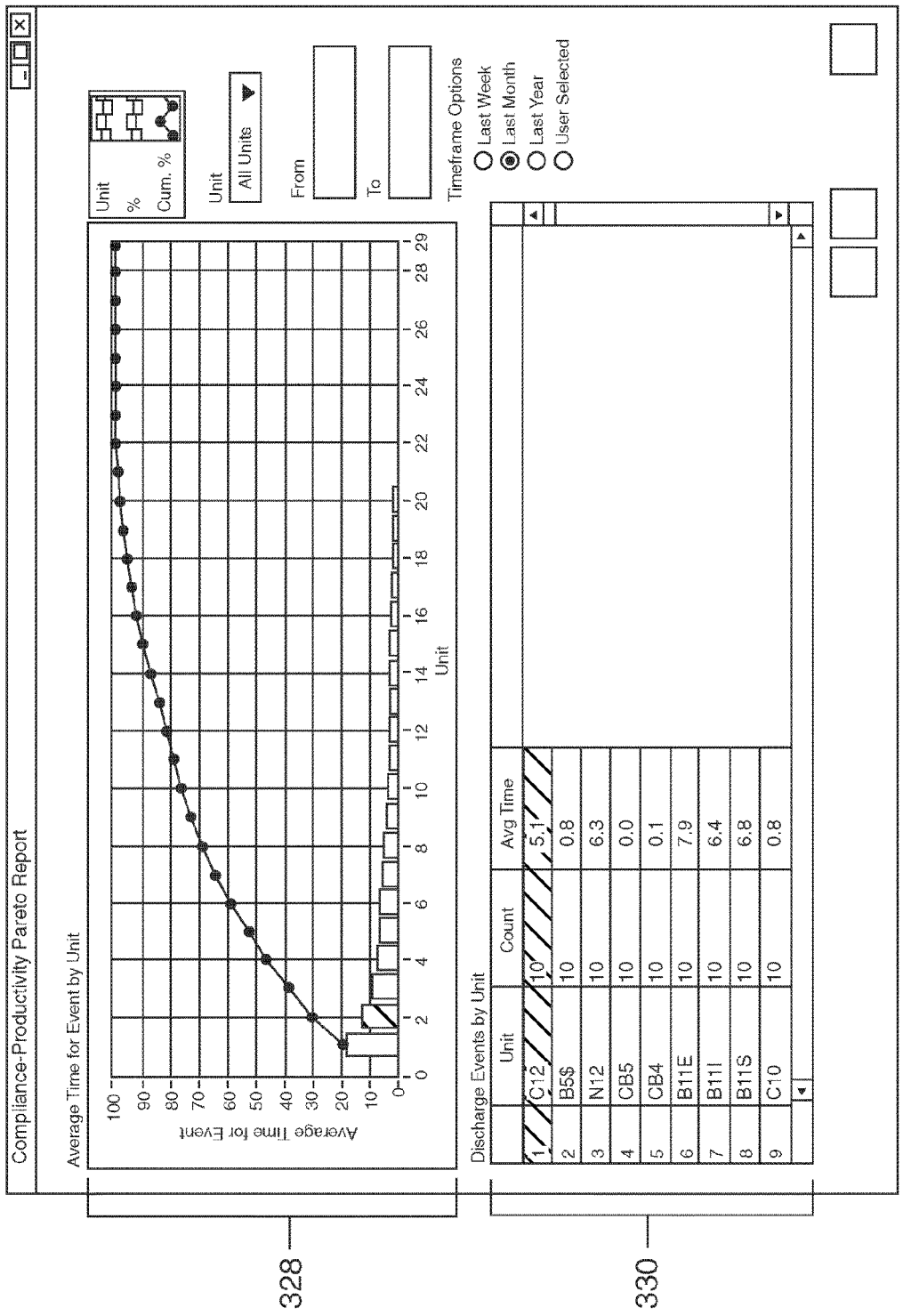

FIG. 34 shows a detailed report generated by the system of the invention for comparing the performance of each unit of a health care facility for performing a selected activity.

Figure 35:
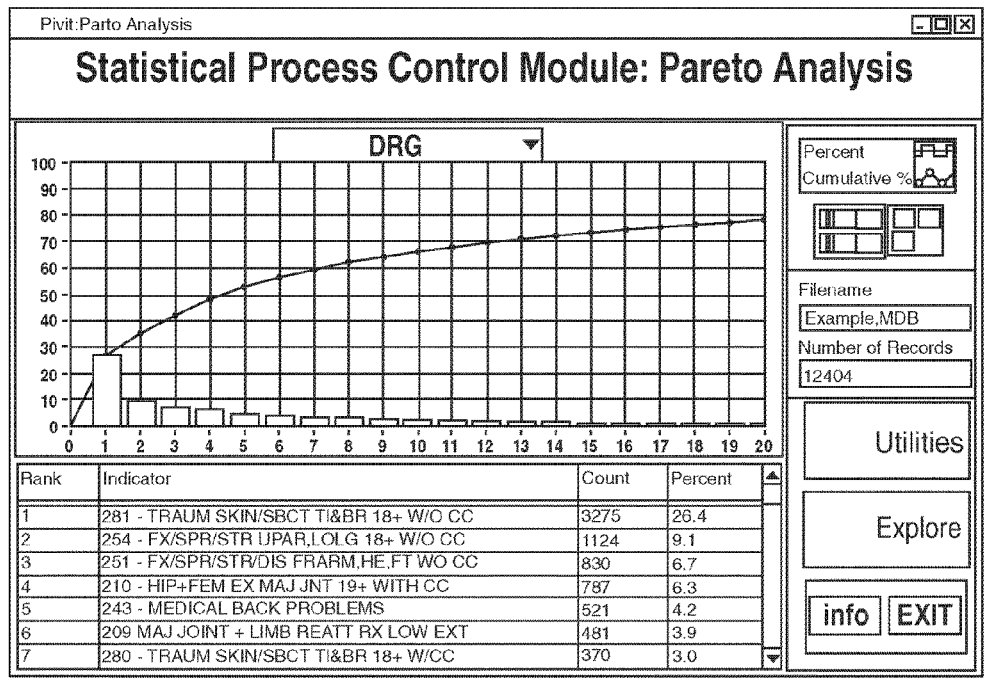

FIG. 35 is a user interface screen generated by the system of the invention illustrating the use of intelligent agents to monitor and notify users of the system of the occurrence of a certain condition related to a health care facility.

Figure 36:
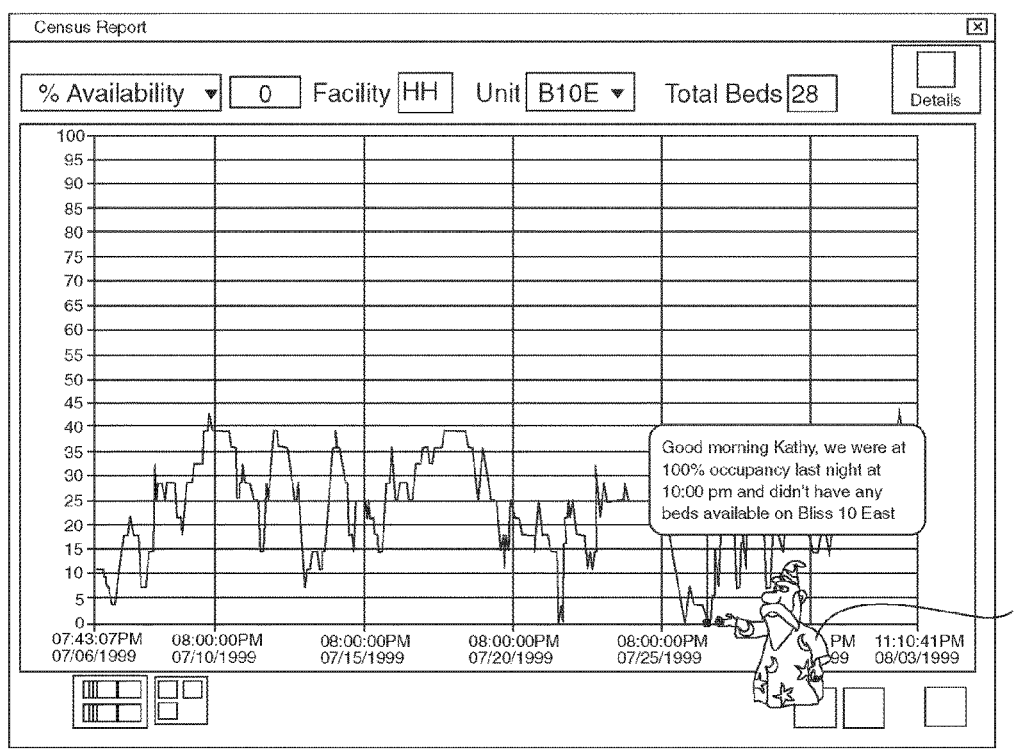

FIG. 36 illustrates an exemplary agent that may be configured to provide notification in the form of on-screen messages.

Figure 37:
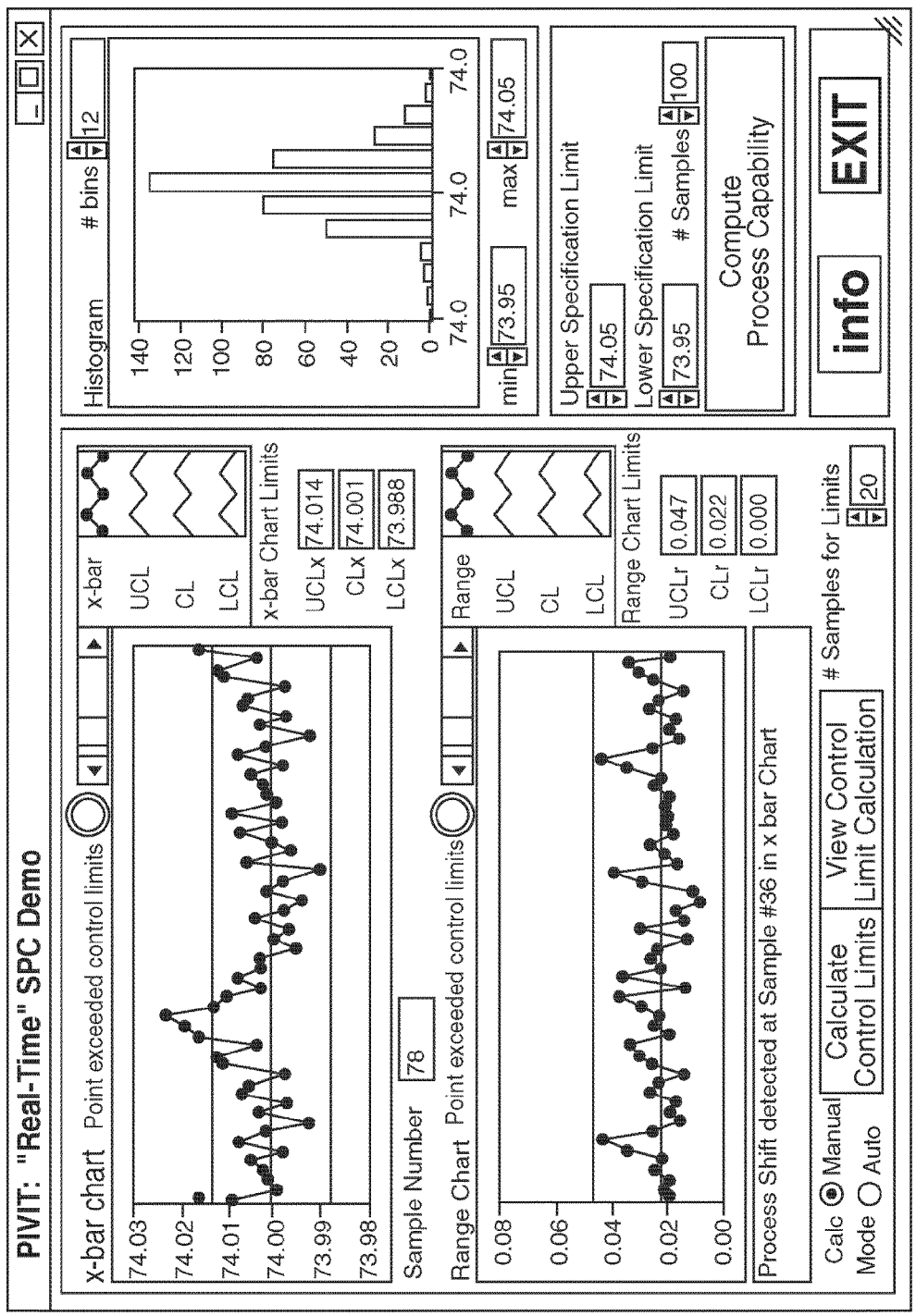

FIG. 37 illustrates another SPC chart that can generated by the data mining and reporting module illustrating a real-time control chart having pre-established upper and lower control limits.

Figure 38:
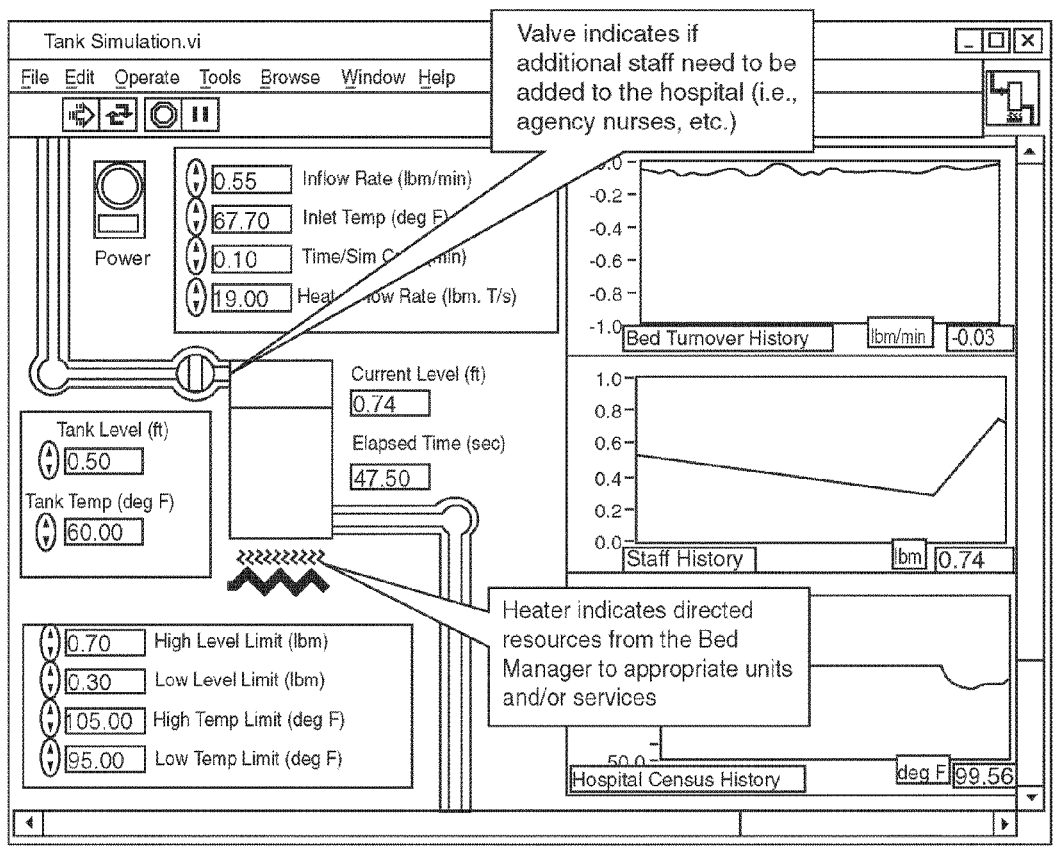

FIG. 38 shows a sample chart showing a tank simulation for a temperature valve.

DETAILED DESCRIPTION OF PREFERRED EMBODIMENTS

Figure 1:
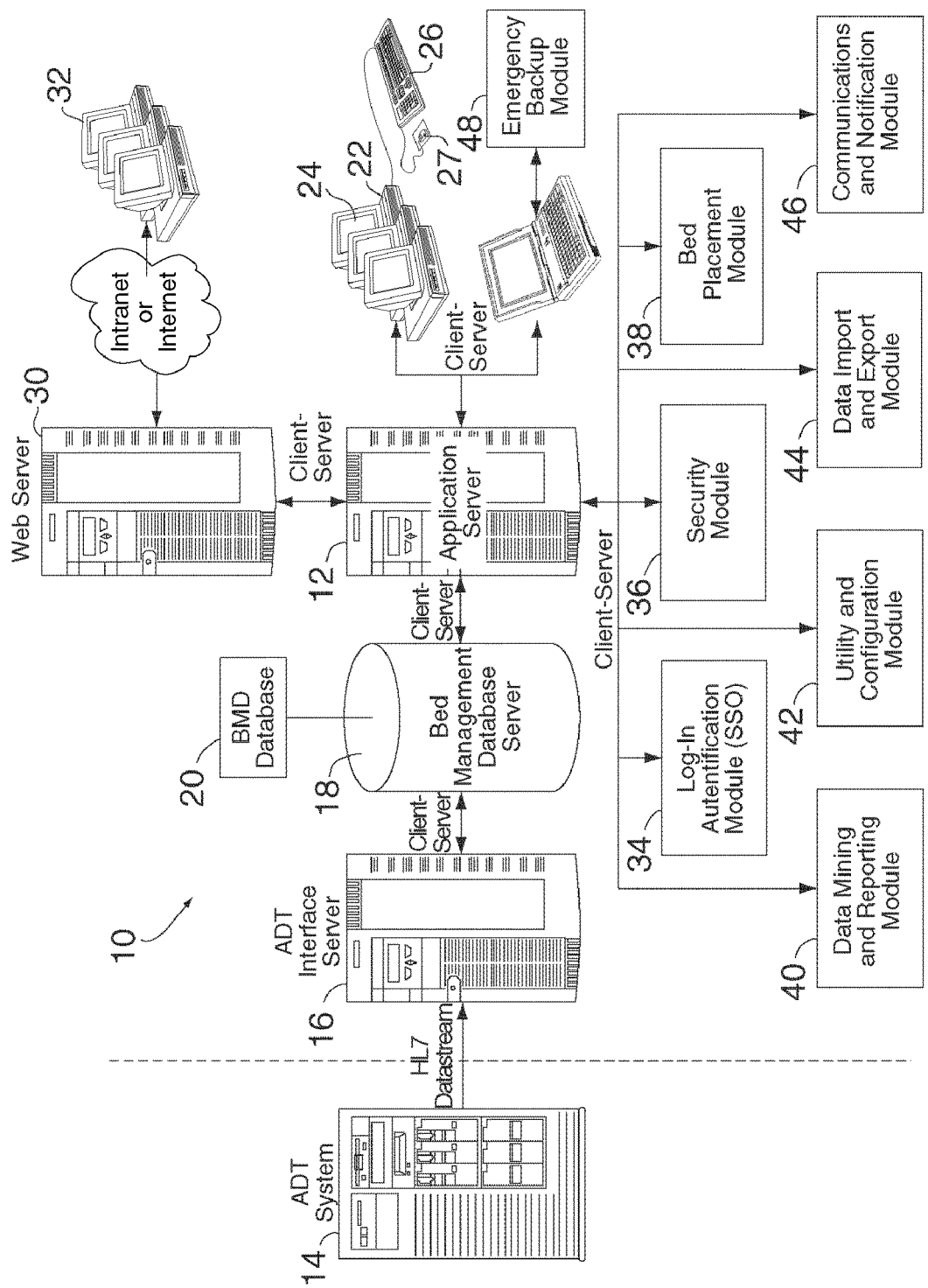
FIG. 1 is a diagram of the preferred embodiment of the bed management system of the present invention.

Referring now to the drawings, FIG. 1 illustrates the preferred embodiment of the bed management system of the present invention generally referred to by the reference numeral 10. The bed management system 10 having a server computer or application server 12 is coupled to an admission/discharge/transfer (ADT) system 14 of a health care facility (not shown) via an ADT interface 16 and a database server 18. The database server 18 having a database 20 coupled thereto. A client computer 22 having a user interface including a display 24, keyboard 26 and pointer 27 is coupled to the server computer 12.

Alternatively, the server computer 12 could be configured as a Web server 30 connectable to client computers 32 via the Internet as illustrated also in FIG. 1.

As will be discussed in detail hereinbelow, the preferred embodiment of the bed management dashboard or bed management system 10 of the present invention includes the following applications identified in FIG. 1 as a log-in module/authentication module 34, security module 36, bed placement module 38, data mining and reporting module 40, utility and configuration module 42, data import and export module 44, communications and notification module 46, and an emergency backup module 48.

Although, the embodiment of the bed management system 10 of the present invention is described herein having an ADT interface for coupling to an ADT system of a health care facility, it should be understood that the present invention bed management system is not limited in this regard and the system interface can be configured to couple the system of the invention to other types of admission systems or networks for health care facilities or in a broader scope of the invention the system can be configured to interface with other types of systems or facilities.

Figure 2:
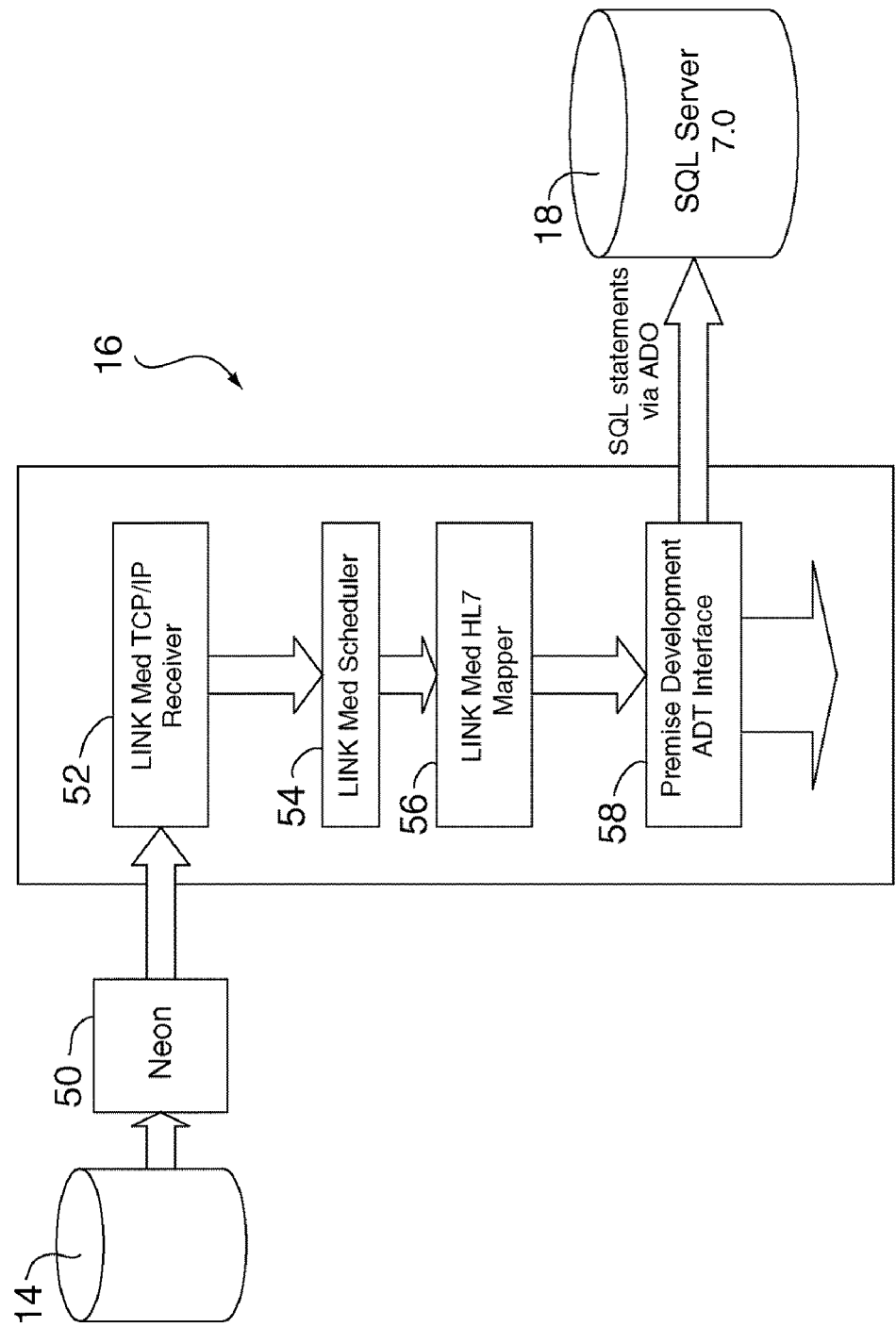
FIG. 2 is a diagram of an ADT interface as used with the present invention.

Referring again to the system 10, FIG. 2 illustrates one embodiment of the ADT interface 16 system interface wherein the database server 18 is coupled to a health care facility's ADT system 14 via the ADT interface 16 and receives patient information therefrom. A Neon Interface 50, (a third party Interface engine) is coupled to and monitors the ADT system 14 for patient transactions and transmits Health Level Seven (HL7) messages consisting of patient information in Transmission Control Protocol (TCP) format to a TCP receiver 52. As shown in FIG. 2, the TCP receiver 52 is a Link Medical Computing, Incorporated of Massachusetts, (LinkMed) TCP receiver. A LinkMed scheduler 54 is coupled to the TCP receiver 52 and is configured to operate approximately every 10 seconds to determine whether or not any new HL7 messages have been received by the TCP receiver. If an HL7 message has been received, an HL7 parser 56 (LinkMed HL7 Mapper), parses the message and extracts therefrom components of the message that are utilized by the bed management system 10.

FIGS. 3 and 4 identify the patient data 60 extracted from an HL7 message and converted to and stored in XML (Extensible Markup Language) format by the HL7 parser 56 for use by the system 10. The data extracted from the ADT system 14 and stored for use by the bed management system 10 includes message data 62 wherein various fields store information related to each ADT message, including the origin, date and time of the message. The extracted data also includes patient ID data 64, which is general identification information for the patient including billing and account information for the patient. Data pertaining to the current visit of the patient to the health care facility is also retrieved from the ADT message and stored as patient visit data 66. Typically, the patient visit data 66 includes detailed information related to the patient's visit including the unit of the facility the patient is admitted to, information related to admitting, referral and attending physicians for the patient's visit, the source of the admission, the date and time of the admission and expected discharge for the patient, etc. In the table shown in FIG. 4, the patient data 60 includes fields for additional patient visit information 68, merge fields 70 for identifying previous patient identification numbers for the patient, as well as clinical data fields and customized fields related to the specific health care facility 72.

Alternatively, the patient data received from the health care facility admissions department can be retrieved, formatted and stored for use of the bed management system 10 using various other methods and configurations, thus the FIGS. 2-4 should be understood as only exemplary representations of the system and methods of the present invention.

Figure 5:
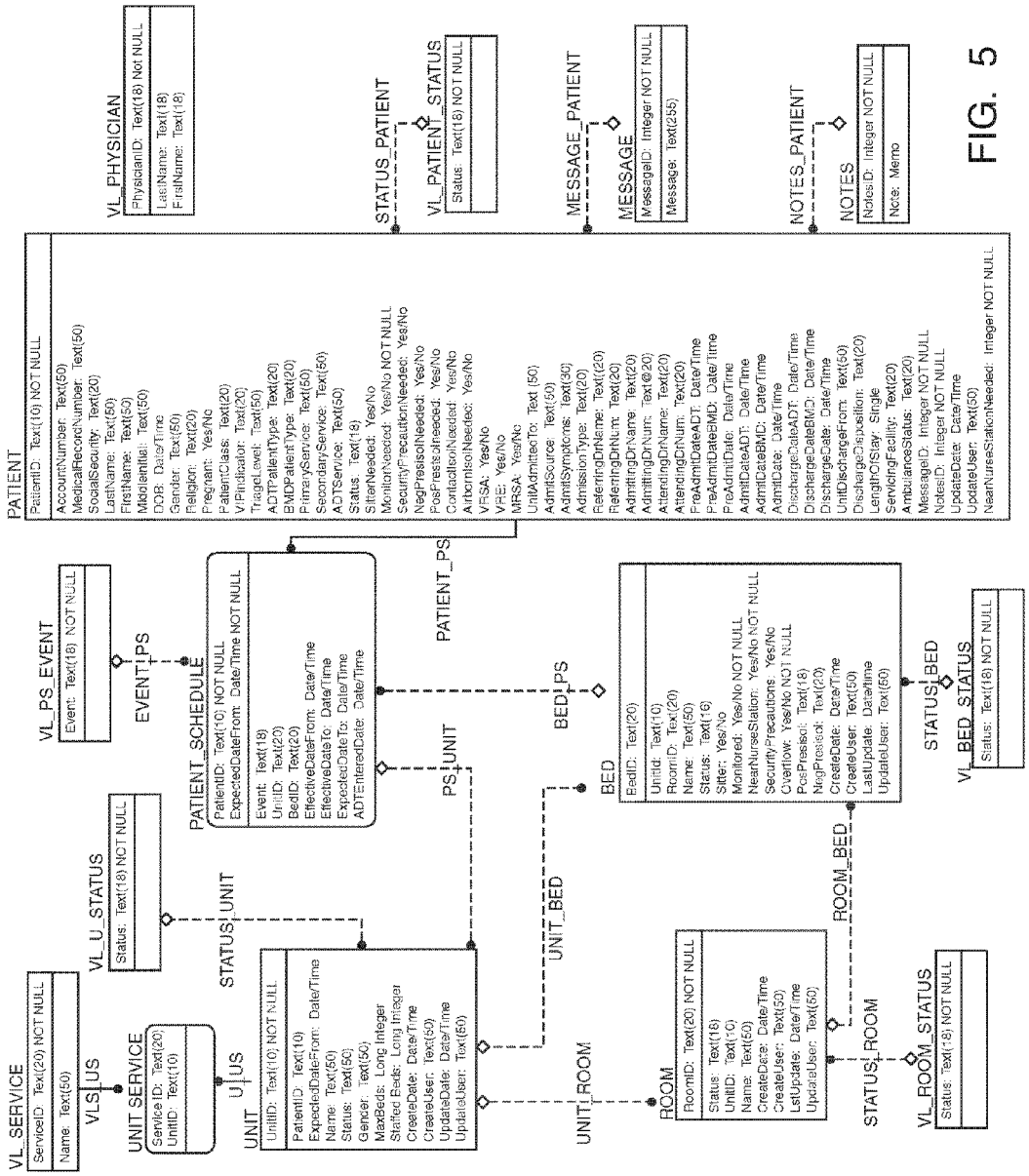
FIG. 5 is a diagram of one embodiment of the database of the present invention system.

An interface 58 is used to process the XML data 60 and store the data 60 in the database 20 for use by the bed management system 10. FIG. 5 illustrates the fields of the database 20. The interface 58 also stores date and time information for the processed HL7 message in a process file (not shown). If the message is flawed or an error occurred during the transmission or processing of the message, the interface 58 is configurable to record the error and transmit an appropriate notification thereof to appropriate administrators for the ADT system 14 or the bed management system 10 of the present invention.

Referring to FIGS. 6A-6Y, the various tables and fields thereof contained in one embodiment of the database 20 are identified. Generally, the data stored in the database 20 is referred to herein as being either "patient data" meaning the data pertains to a patient, or "bed attribute data" wherein the data pertains to the attributes of the beds, or the health care facility. The data stored in the database 20 includes the patient data 60 retrieved from the health care facility as discussed above, and data that pertains to the facility, the beds, the staff, etc. The stored data is formatted such that the bed management system 10 is capable of accessing and updating many different data fields related to the patient, the beds in the facility, the bed occupancy levels, the performance of the staff, etc.

etc. as well as current, historical, and future information associated with the operation of the hospital.

As shown in FIG. 6A, the database 20 includes information related to the attributes and status of each bed in the facility. FIGS. 6B and 6C illustrate data tables wherein messages and notes related to a patient, the patient's visit in the health care facility or the facility itself are identified and stored in the database 20. FIG. 6D illustrates a patient table shown that includes general information regarding the patient and requirements for the patient's care during the current hospital visit. Schedule information for the patient is stored as shown in FIG. 6E. FIGS. 6F-6I show tables for storing information related to the rooms and units of the health care facility as well as other miscellaneous information for use by the bed management system 10. FIGS. 6J and 6K illustrate exemplary tables for storing information related to various attributes of the facility and the attribute value respectively. Similarly, FIG. 6L illustrates a table in database 20 for storing a bed attribute and the value thereof. Bed attributes include whether the room is positive or negative pressurized, whether or not the room has security or VIP capabilities, if the room is designated a male or female room or a unisex room, if the room is a private room, semi private, etc. The status of the beds and rooms are also stored in the database 20 as attributes such as whether or not the room is available or if the room has been cleaned or is scheduled to be cleaned as well as if the room is out of service for mechanical reasons such as the air conditioning or bathroom facilities are in need of repair, etc.

FIGS. 6M-6P illustrate tables of database 20 for storing events, patient attributes, room attributes and unit attributes. FIGS. 6Q through 6W illustrate tables of the database 20 for storing archived data related to events, patients, beds, units, as well as other information useful to the bed management system 10 for monitoring and managing the performance of a health care facility. Also stored in the database 20 is information related to the staff and status of the rooms and units of the health care facility such as the number of employees assigned to a unit of the facility.

Thus, the database 20 stores all relevant information required to manage the patient bed assignments and the bed occupancy of the health care facility for normal operation as well as in emergency situations such as when a large number of beds are needed on short notice.

FIG. 6X illustrates a unit security table where security information is stored for controlling user access to the database 20.

FIG. 6Y shows a patient stay table of the database 20 wherein information related to the patient's stay in the health care facility is stored.

Additionally, the database 20 may include additional tables similar to the Patient_Schedule Table (FIG. 6E) and Patient_Stay Table (FIG. 6Y) for storing historical data such that the bed management system 10 can provide better and faster access to data and reports regarding previous visits to the health care facility for a patient as well as the status of the facility at that time.

The database 20 is updated by the database server 18 throughout the operation of the system in response to requests by system administrators, authorized users, the server computer 12 or in response to messages from the ADT system 14 or other client requests.

The system 10 includes an emergency backup module 48 wherein a second database (not shown) is maintained for parallel storage of the data stored in the database 20. The second database is connectable to a backup server for operating the system 10 and recovering the data in the database 20 in the event of a malfunction of the system 10.

Additionally, the system 10 provides monitoring and reporting capabilities for monitoring the occurrence of certain symptoms or diseases or other parameter which may be relevant in an emergency situation or for research or other purposes. The system is configurable for monitoring, reporting, comparing, etc. any parameter or function thereof of the data stored in the database 20. This feature is also useful in a bed management system 10 configured to operate in conjunction with a plurality of health care facilities.

Referring again to FIG. 1, the bed management system 10 includes a log-in authentication module 34 for processing user log-in requests for the bed management system. The authentication module 34 can function independently of the health care facility network and assign and utilize individual user login identification and passwords that are stored in the database 20 for each user of the bed management system 10.

Figure 8:
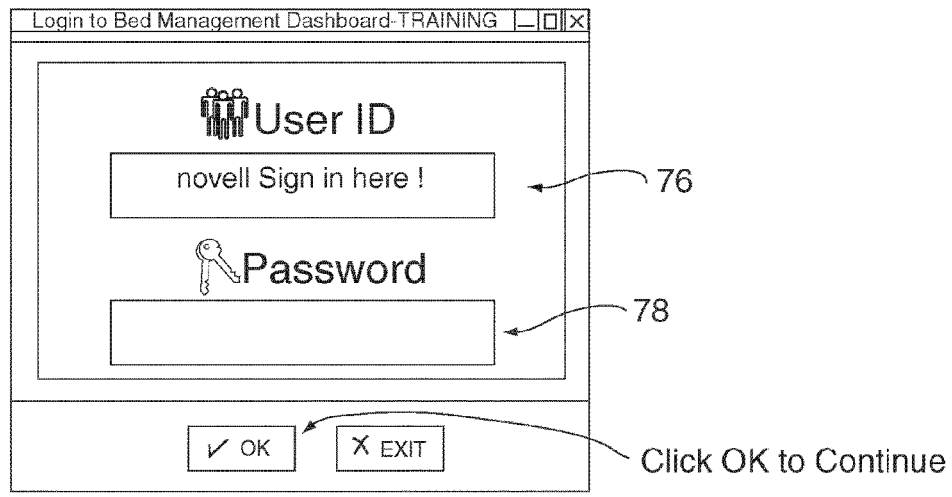
FIG. 8 is an illustration of a login screen as used by the bed management system of the present invention.

Alternatively, as in the preferred embodiment of the bed management system 10, the login module 34 is coupled to the health care facility's network such that the health care facility's login system is used to authenticate a user's request to access the bed management system 10. Referring to FIG. 7, a Novell® LDAP server 74 is utilized by the health care facility for user authentication and the bed management system 10 is coupled thereto, such that a user can access the bed management system 10 using the same login identification name and password as he/she uses for access to the Novell® network of the health care facility. A typical login screen as displayed on a client computer 22 of the bed management system 10 is illustrated in FIG. 8 wherein a user's is prompted to enter a Novell® user ID at 76 and a password at 78. Additionally, the login module 34 can be configured to track and store data as to the use of the client computers 22 including all users, logins and logouts for the system 10.

Additionally, a security module 36 shown in FIG. 1 is coupled to the server computer 12 for controlling user access to the bed management system 10 as well as tracking all user activity within the system. The security module 36 is configured to provide various levels of security for using the system 10, including task level security, attribute level security, and attribute value level security wherein actions performed in using the system are referred to as tasks and each task has various attributes associated therewith. The security module 36 is configured to associate each user with a specific role, thus the levels of security in the system are based on the role of the user rather than the identification of the individual user, however, a user can be associated with multiple roles.

In using the bed management system 10 each task or attribute thereof is permitted only by users in certain roles, thus prior to executing a user requested task, the security module 36 verifies the role of the user and confirms that a user in that role can perform the requested task. Examples of task identifiers used with the security module 36 are:

module—does the user have the authorization to enter this module of the system, e.g. login module 34, security module 36, etc.;

screen—can the user view a screen, e.g. health care facility summary screen; task—view physician roll-up values;

action—use a pull-down to select various columns in a screen;

process—assign a patient to a bed;

indicator—view an indicator, e.g. hospital occupancy level indicator.

Thus, the security module 36 controls the use of the bed management system 10 on a task by task basis, wherein authorization for each requested task is verified based on the role of the user before the task is executed. The security module 36 is variably configured to ensure that the system 10 satisfies HIPPA requirements including those related to patient privacy.

Figure 9:
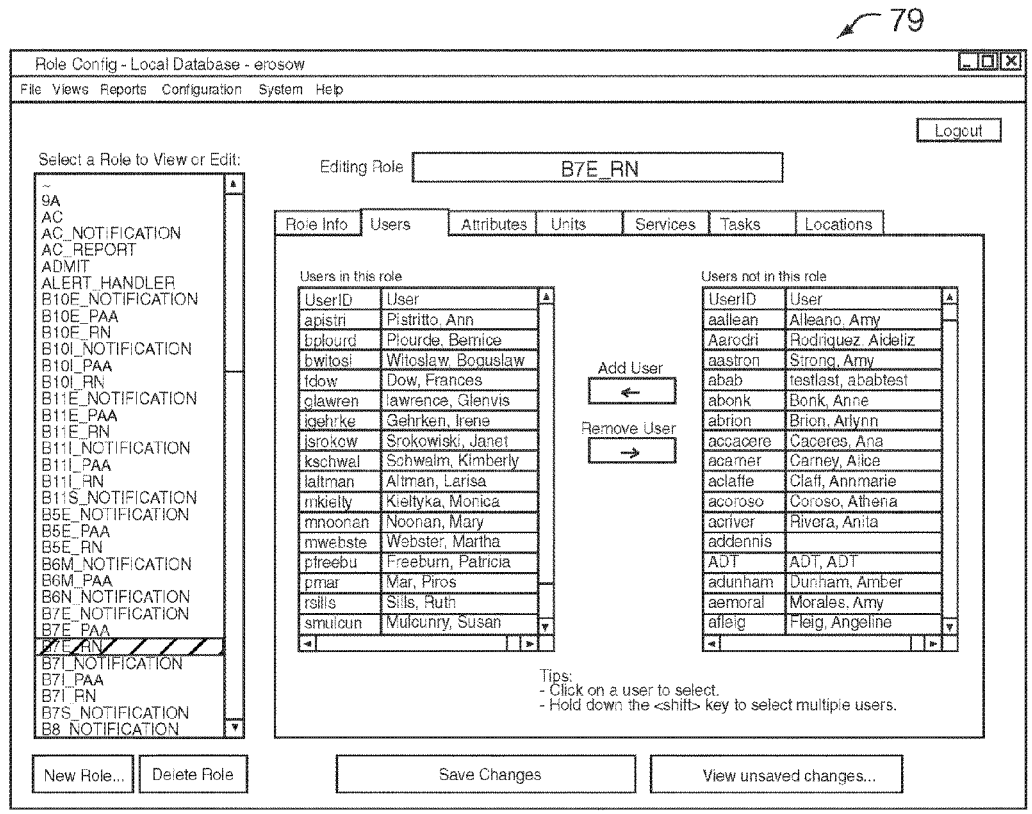
FIG. 9 is an illustration of a role configuration screen as used for configuring the system of the present invention.
Figure 10:
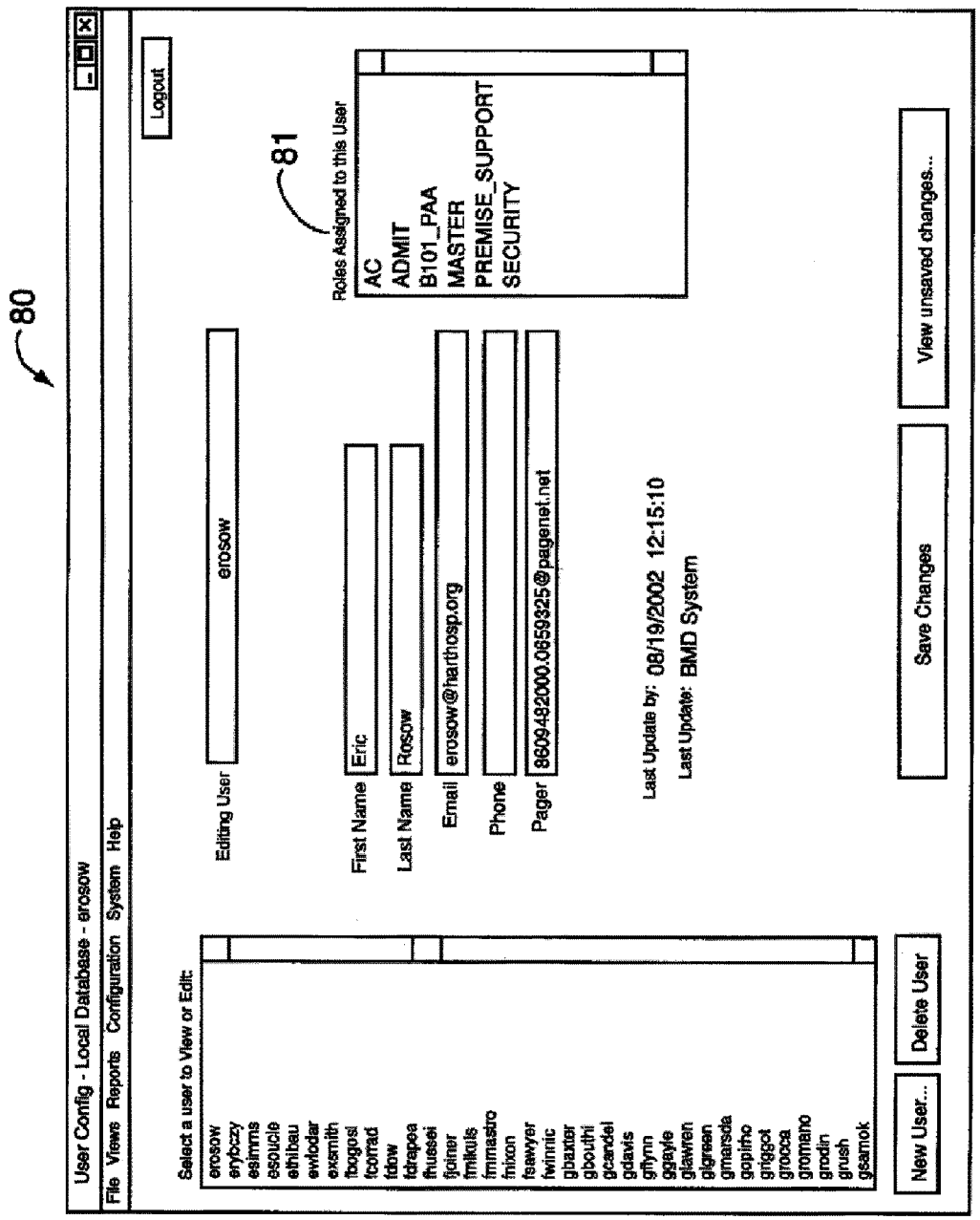
FIG. 10 is an illustration of a user configuration screen as used for assigning roles to a user of the bed management system.

FIG. 9 illustrates a role configuration screen 79 accessible from the utility configuration module 42 shown in FIG. 1. Using the screen 79, administrators of the bed management system 10 can configure users within each role and define authorized tasks for each role. Similarly, FIG. 10, shows a user configuration screen 80 also accessible through the utility configuration module 42 for configuring the roles of specific users of the bed management system 10. As shown at block 81, one or more roles can be assigned to a particular user.

The utility and configuration module 42, shown in FIG. 1 is coupled to the server computer 12 for the use of administrators of the bed management system 10 to control and configure the operation of the system. The utility and configuration module 42 includes diagnostic screens and self-checking status indicators for maintaining the operation of the system. Additionally, the module 42 includes control panels for reviewing the status of active users, for creating administrative messages to be forwarded to users of the system and for configuring the system for security purposes including user and role security as discussed above. The utility and configuration module 42 is also utilized to configure the system as to the conditions monitored by intelligent agents as well as all other user defined attributes of the bed management system 10 as will be discussed further hereinbelow.

Figure 11:
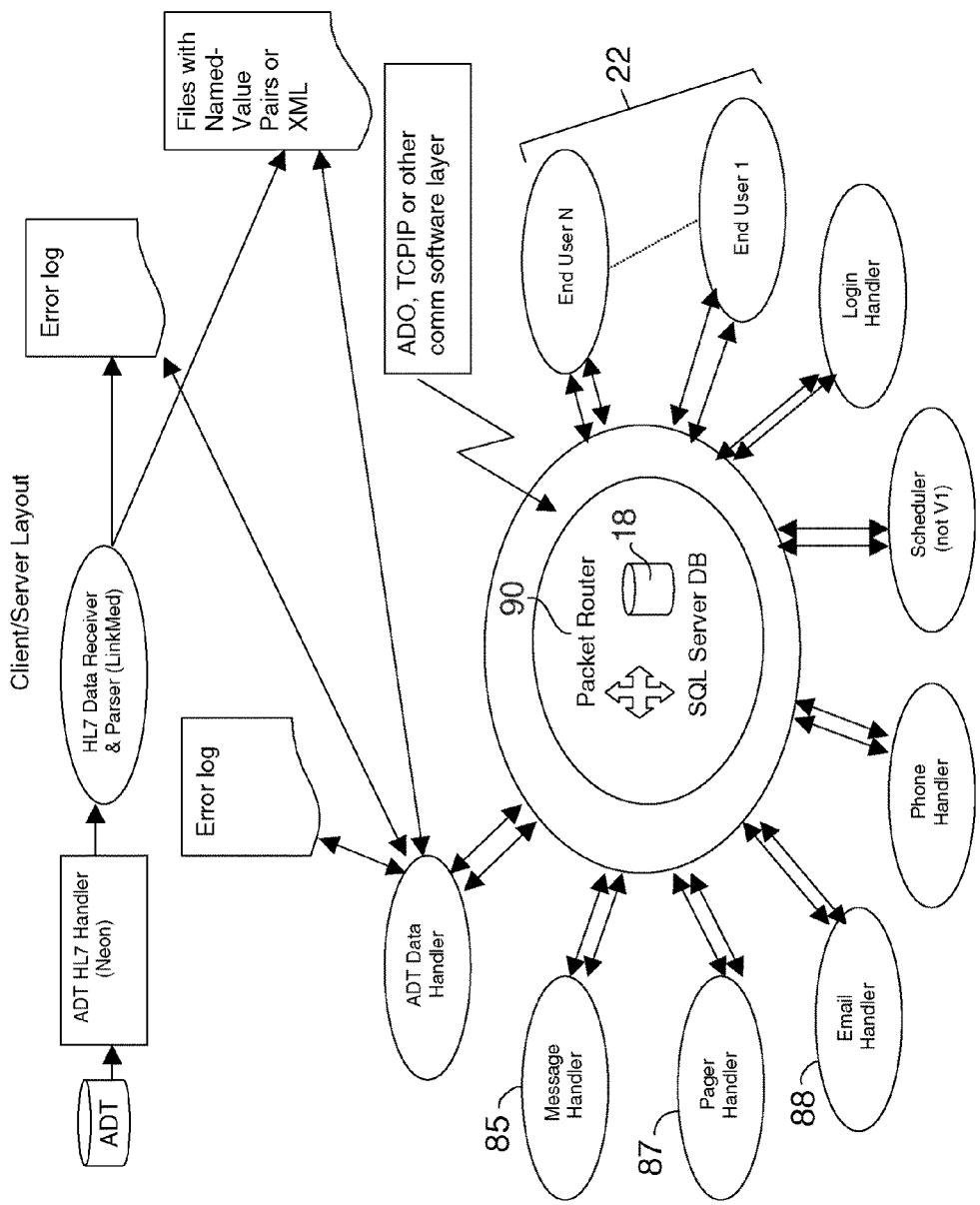
FIG. 11 is a diagram of one embodiment of communications and notification system of the present invention.

Referring to FIG. 11, one embodiment of the bed management system 10 is shown illustrating the communication system thereof. The system 10 includes a message handler 85 for processing all messages and notifications for the system 10 including user notifications such as emails, fax messages, telephone calls, pagers, pop-up windows, etc. In the FIG. 11 embodiment, the message handler 85, includes a separate application to process messages of each type, such as pager handler 87, Email handler 89, etc. Notifications include all messages forwarded to a user such as screen messages, messages sent to a user's email address or messages sent to a user's pager. The message handler controls all notifications and acknowledgements thereof. The message handler determines when a notification should be sent, how many times to send the notification as well as how the notification should be sent. Each user and user role has variably configured sets of Notify Methods configured via the utility and configuration module 42 such that the message handler knows how to forward any notification to each user or role. All communications between clients are processed through a packet router 90. Upon creation of a message it is stored by a packet router 90 in the database 20 and the message handler is notified that a new message has been created. If a message is destined for delivery to a role, each user logged in with the role is sent the message. The packet router 90, packets all messages and forwards each to the proper recipients as well as sends and receives acknowledgments (ack/nak) for each message to and from the recipients thereof. FIG. 11 shows the database server 18 and the packet router together, however it should be understood that this arrangement is not necessary.

A data import and export module 44 is provided to facilitate the importing and exporting of data to/from external devices and applications. For example, the bed management system 10 is configurable to access and import data and applications from web servers or other external devices in the health care facility or related thereto. For example other ancillary health care systems, such as clinical information systems that contain electronic medical records for a patient, clinical flowsheets, severity adjustment documents and other types of information can be integrated and processed by the bed management system 10 via the data import and export module 44.

Additionally, the system can interface through the data import and export module 44 with other external systems such as nurse call systems wherein the bed management system is configured to assist or provide processing, monitoring, notifications of all activities related to and provided by nurse call systems. For example, if the bed management system 10 is coupled to the nurse call system of the facility, the data mining and reporting module 40 can be can monitor and report patient wait time for nurse calls, average response time by unit during a specific time period, etc.

The data import and export module 44 can also be used to couple the bed management system 10 to patient transport systems, housekeeping systems, food preparation or kitchen service systems for monitoring, reporting and control of ancillary services related to the health care facility. These systems can be interfaced with the bed management system 10 using various methods including intelligent voice recognition technology and tools therefor. Additionally, the system 10 is connectable to interactive TV systems of a health care facility, wherein a patient via the room TV can submit patient requests to the bed management system 10 for processing. Examples of patient requests of this type are typical nurse call requests such as food, water, bed cleaning requests, requests for assistance to use restroom or shower facilities, etc.

Also, the data import and export module 44 of the bed management system 10 can be configured to couple to other external devices and systems such as patient monitoring networks for example General Electric Medical Systems UNITY Patient Monitoring Network that monitors a patient's vital signs such as EKG, heartrate, oxygen saturation, blood pressure, etc. on a 24 hour basis.

Once logged in to the system, the system can be used in various ways depending on the role of the user. For example, the bed placement module 38 shown in FIG. 1 provides user and client access to information stored in the database 20 related to patient bed assignments and bed attribute information related thereto. The function of the bed placement module 38 includes providing user access to dynamic and interactive sortable user interface screens such as the one shown in FIG. 12.

Figure 12:
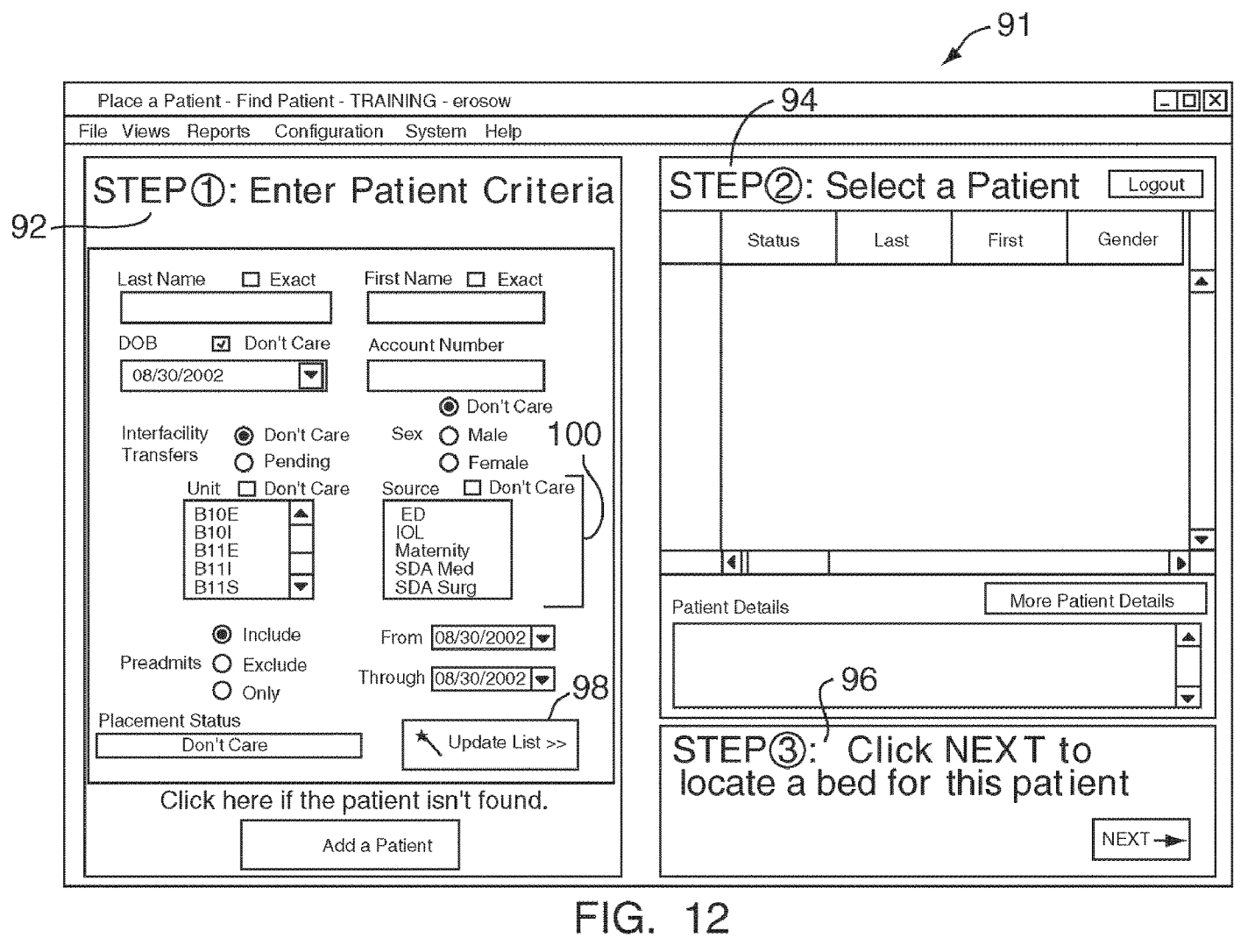

Referring to the user screen 91 shown in FIG. 12, the bed placement module 38 assists a user to assign a patient to an appropriate bed in the facility by guiding the user through a set of process screens that are used to identify and select an available bed that meets the specific needs of an individual patient. The user screen 91, Place a Patient—Find Patient screen, identifies three steps; step 1 at 92, step 2 at 94, and step 3 at 96 that provide user friendly access to the data stored in database 20 for locating an available bed for a particular patient and assigning the patient to the selected bed.

Referring to step 1 at 92, the user first enters various criteria to identify the patient. These criteria include the patients, last name, first name, date of birth or account number, for example. The criteria may also be of a general nature, such as by patient status, pre-admits through a desired time period, or the type of medical service. By clicking the update list button 98, a user request is transmitted to the server computer 12 and the system 10 performs a search of the database 20 and returns a list of all patients meeting the specified criteria. The search is limited to the source field indicated at 100 (in this case, the Emergency Department, ED). The search may produce a plurality of patients as shown at 102 in screen 104 shown in FIG. 13.

Figure 13:
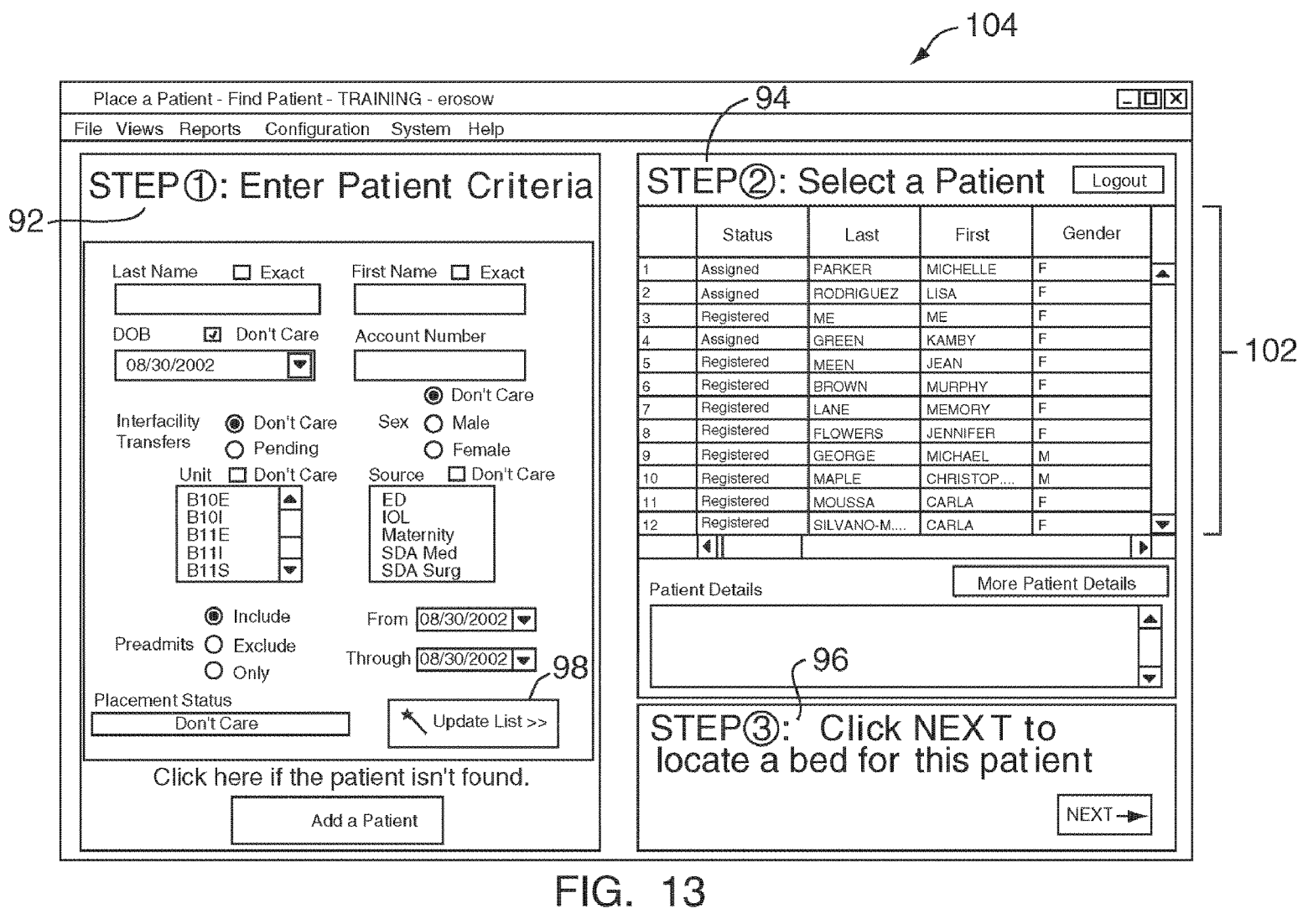

Referring to FIG. 13 at block 102, the system displays a sortable list of all of the patients meeting the specified criteria. The profiled list of patients 102 is sortable by status, last name, first name, gender, birth date, symptoms, diagnosis, arrival time, and every other one of the variable data fields included in the user display. The fields are variable such that all patient data available in the database 20 can be included in a sortable field of a user screen.

Figure 14:
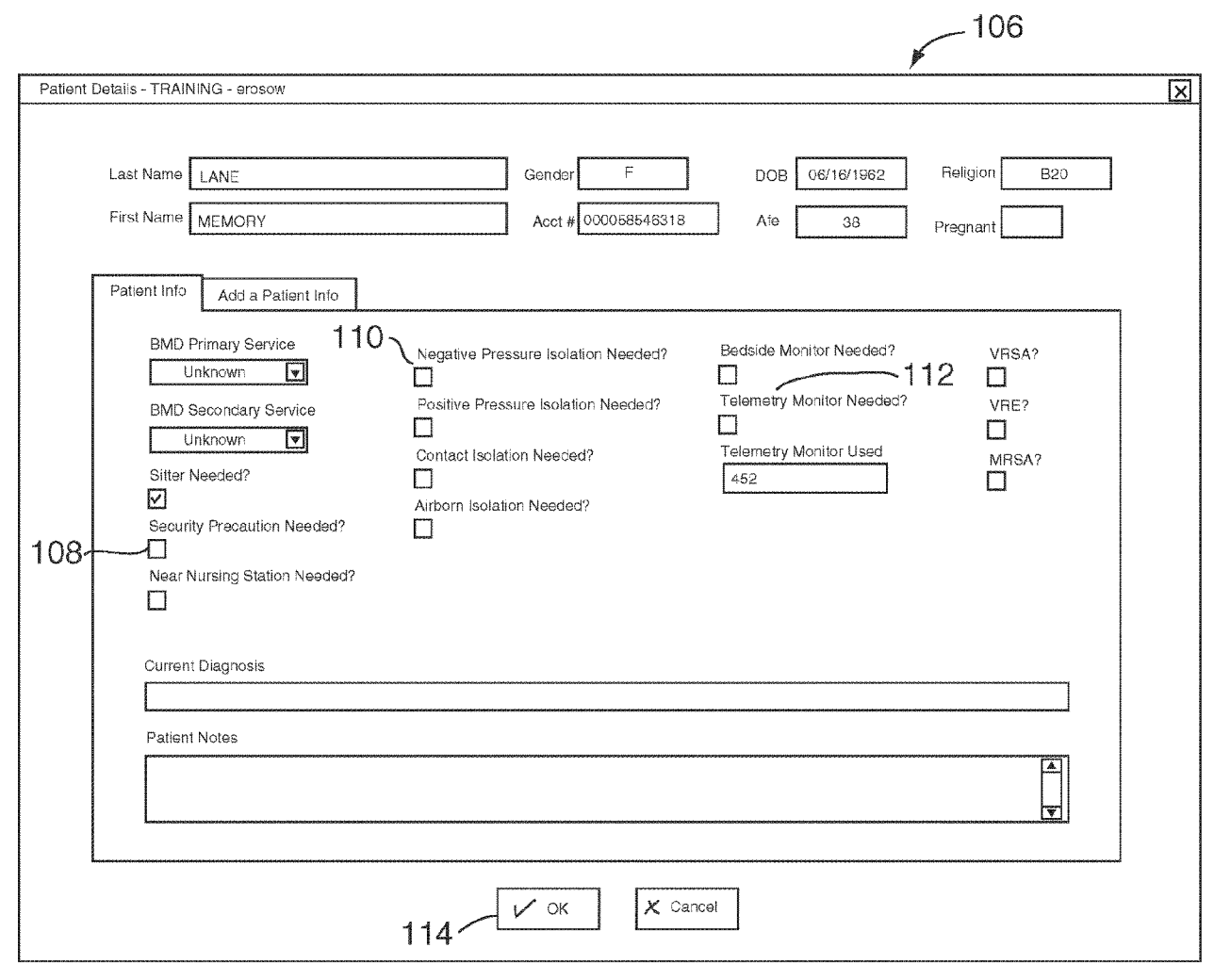

Referring to FIG. 14, a patient details screen 106 can be accessed by clicking on the name or row of a desired patient using the pointer 27 in the screen 104. The patient details screen 106 is populated by the bed management system 10 using the patient data from the database 20. Alternatively, a user having the proper authorization, as will be discussed hereinbelow, can view, enter or update the patient data accordingly. For example, if the patient is a security risk, indicated at 108, if the patient requires a negative pressure room 110, if the patient requires a telemetry monitor 112, (shown as required in screen 106), etc. By clicking the OK button 114, the bed management system returns to display the previous screen 104, shown in FIG. 13 as well as updates the database 20 accordingly as to the user updated information for the patient.

Referring again to FIG. 13 and the user screen 104, a user can continue with the bed assignment process by clicking the NEXT button at 96, after selecting a patient to be assigned to an appropriate bed. The system 10, then displays the screen 1, Place a Patient-Find Bed, shown in FIG. 15, where an available bed can be identified and requested.

Figure 15:
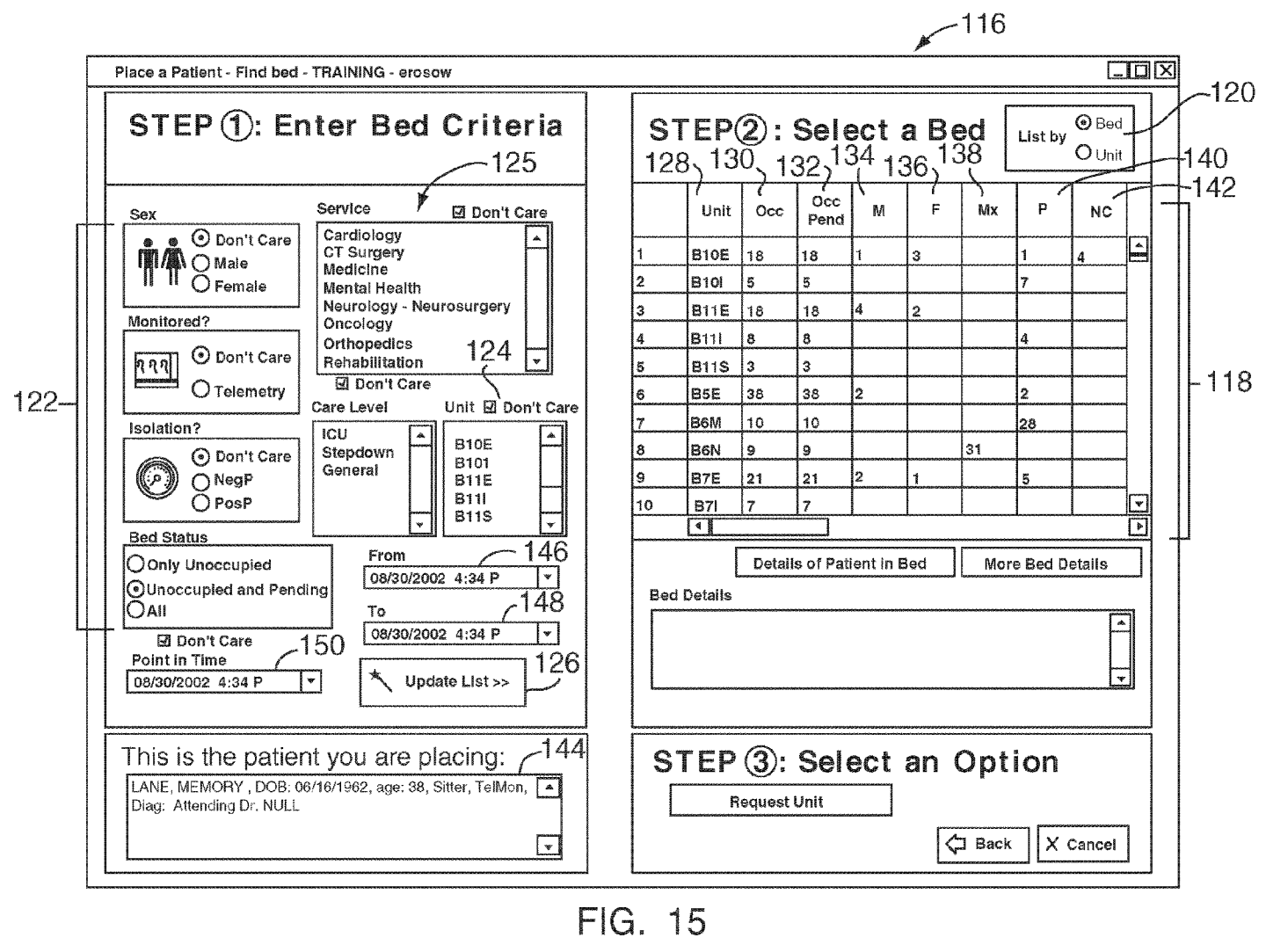

Referring now to FIG. 15, the Find Bed screen 116 is illustrated wherein the available beds are profiled in a unit view at 118, that is selected using the view indicator at 120. Notice a bed view portion of the screen 122, is darkened and not activated in the unit view. As shown, the user has chosen to view all the units in the healthcare facility as indicated by the Unit Don't Care box 124 being checked. Additionally, the occupancy of the health care facility can be viewed based on a service group as shown at block 125. The update list button 126 issues a client request to the server computer 12 to access and query the database 20 and update the data fields in the screen 116 accordingly. In the unit view 118 selected, current occupancy data for the entire health care facility is accessed in sortable tables. For example, the particular unit of the health care facility is identified at 128, the current occupancy of the unit at 130, the pending occupancy at 132 includes detailed information for pending incoming and pending outgoing patients to the unit. The number of male beds in the unit is indicated at 134, number of female beds at 136, number of mixed beds at 138 (i.e., both male and female beds such as on a unit for newborns), private beds at 140, the number of non-committed beds at 142, (i.e., 2 beds that are in a semi-private room, neither of which is occupied are non-committed beds, however once one is occupied by a female for example, then the remaining unoccupied bed is designated also as a female bed). Also, identified although not shown in screen, are the number of negative pressure beds, positive pressure beds, as well as the number of monitored beds including hardwired monitors and telemetry monitors. Additionally, information regarding the selected patient for the bed assignment is identified including patient requirements in the Find Bed screen 116 as shown at 144.

The bed management system 10 includes the capability to view the current occupancy level of the facility as well as predictions for the occupancy level of the facility at future points in time. Future points in time as well as ranges thereof can be entered at the From and To blocks 146 and 148 respectively and the point in time block 150. As mentioned above, each column in the screen 116 shown in FIG. 15 is sortable by clicking on the column heading.

Figure 16:
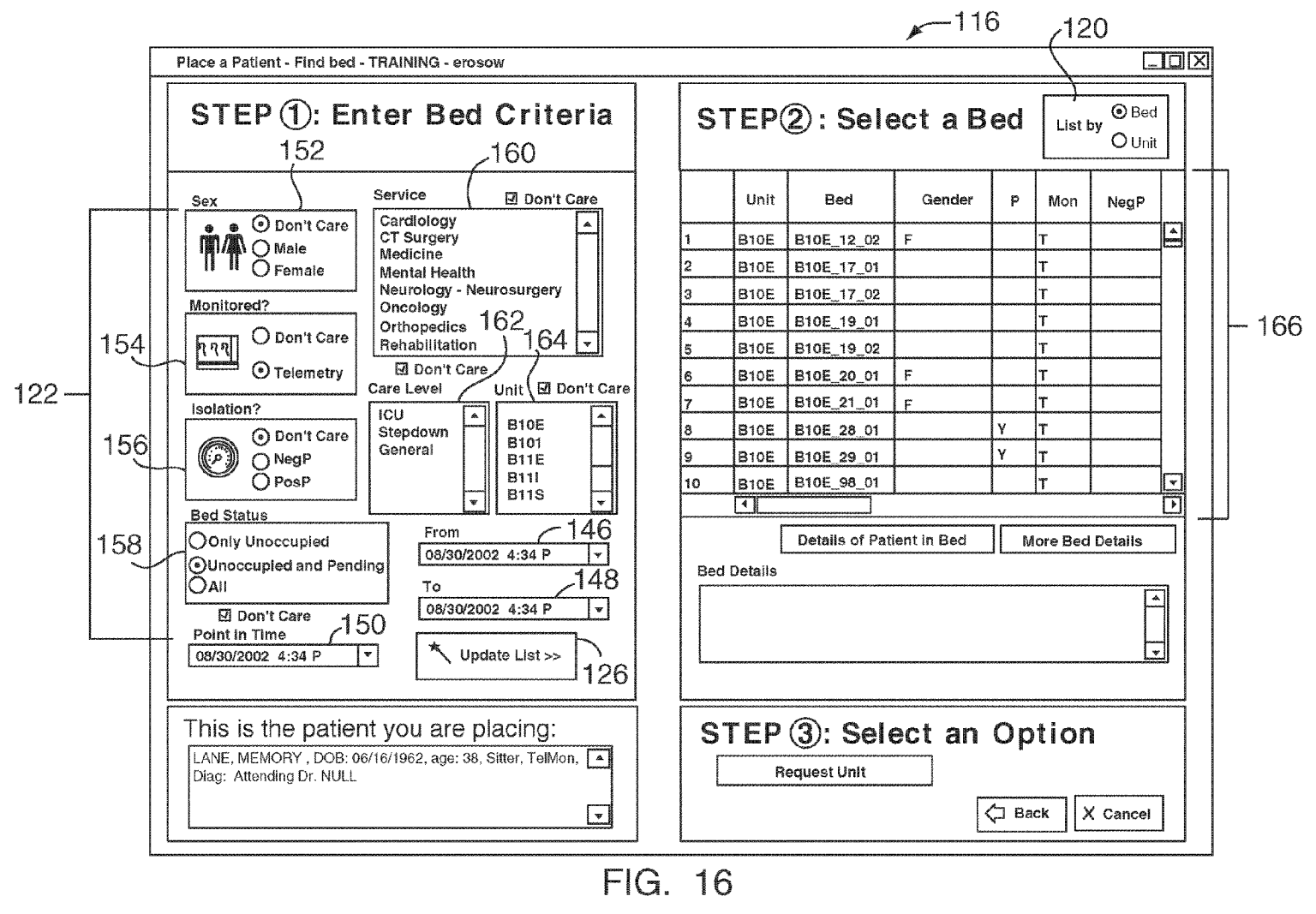

Referring now to FIG. 16, the Find Bed screen 116 is illustrated wherein the available beds are profiled in the bed view 122, selected using the view indicator at 120. In this mode, the bed placement module 38 provides user controls for selecting the bed sex at 152, the monitoring capability of the bed at 154, isolation attributes for the bed at 156 and the current status of the bed at 158. Additionally, the user can specify the bed by service group at 160, the level of care at 162, as well as a particular unit at 164. Additionally, the Find Bed screen 116, allows the user to query the database 20 for current available beds or for future availability by selecting a point in time at block 150 or a range thereof using the From and To blocks, 146 and 148 respectively.

Still referring to FIG. 16, by clicking the update list button 126, the user initiates a query of the database 20 wherein the system returns a list 166 of all beds meeting the selected criteria. The user may select a bed from the list by clicking on the proper row in the list at 166.

Figures 17, 18:
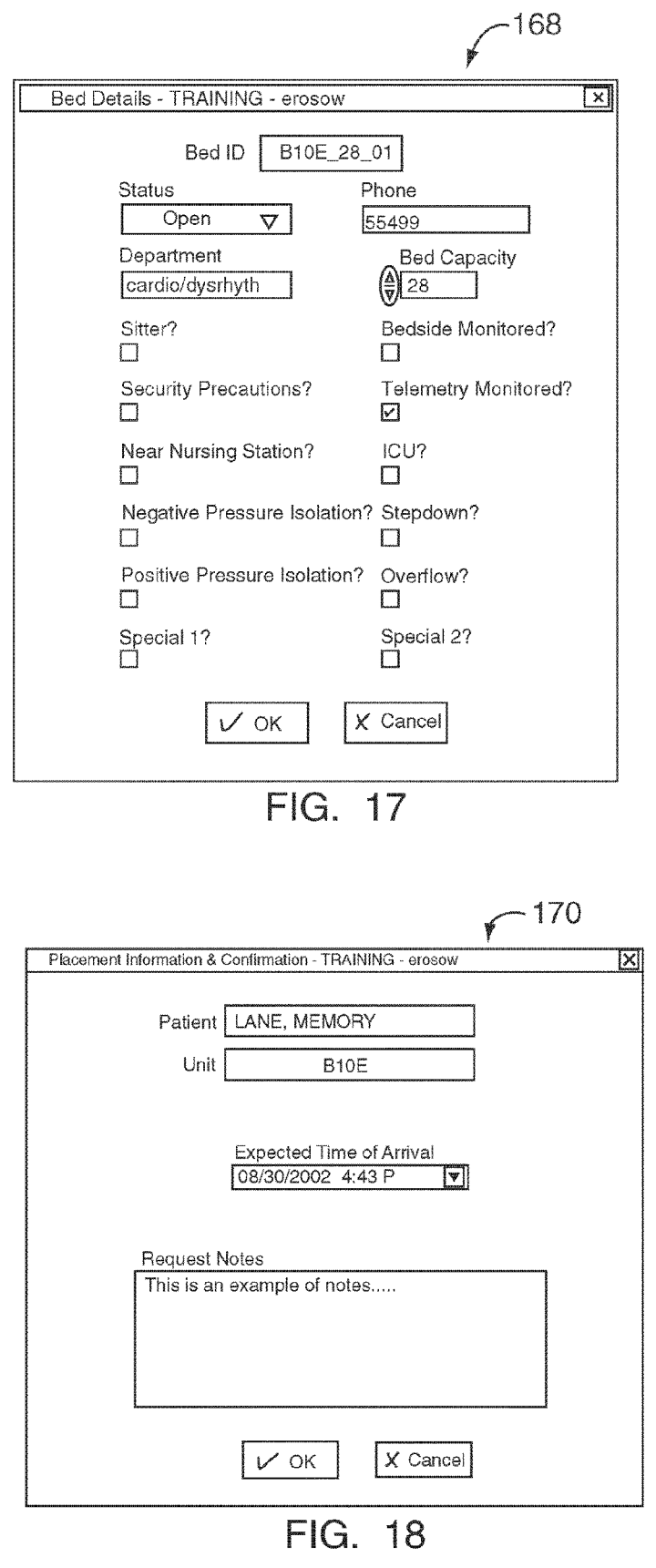

A user may specify additional bed requirements using the screen 168 shown in FIG. 17. Once an appropriate bed is selected, the user is notified with a pop-up screen 170 as shown in FIG. 18 wherein the name of the patient is confirmed, the selected bed ID, the expected arrival time for the patient and a field where any notes regarding the admission or otherwise may be entered. User confirmation of the placement information and confirmation screen 168 activates transmission of a message to be forwarded to the appropriate staff on the unit where the selected bed is located. The above-identified process for assigning a bed to a patient takes approximately 15 seconds for a user to complete.

The system 10 provides user friendly attributes throughout the system, for example, once a patient is assigned a bed, the patient's name displayed changes in color from red to black as well as a reserved column (not shown) being updated to indicate the patient has a bed reserved.

Figure 19:
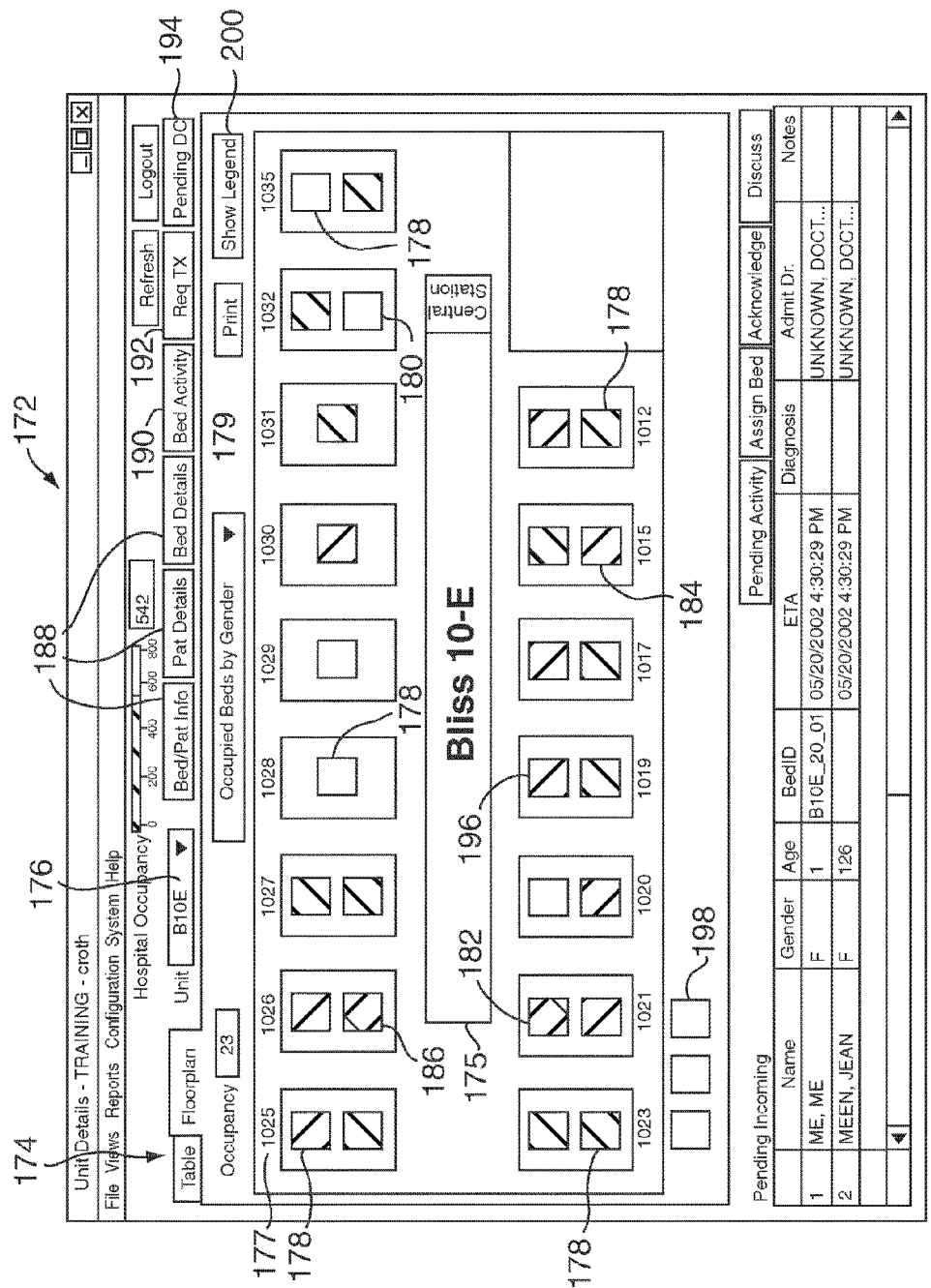
FIG. 19 is one embodiment of an interactive user interface for the system showing a unit detail in a floor plan view.

The bed management system 10 provides a plurality of interactive user screens containing data tailored to the needs of a particular user or user role. FIG. 19 illustrates an exemplary embodiment of how patient information can be viewed in a dynamic and interactive Unit Detail—floor plan mode, shown in screen 172. The unit details can also be viewed in a table mode using the tab at 174. In the embodiment depicted, there is shown a graphical view of an intensive care unit, namely Bliss 10-E identified at block 175. Views of other units can be viewed using the pull-down indicator at 176. The room number for each room on the unit is identified at 177 and each bed is presented as a square icon, generally referred to by the reference numeral 178, in a simplified floor plan view of the unit. In a preferred embodiment, colors are used to indicate the selected attribute of the patient or bed. For example, the display in FIG. 19 may be configured to show available beds using icons 178 in green and occupied beds in red. Additionally, the bed icons can be viewed in different colors depending on the attributes of the beds displayed. For example, the pull down selector 179 allows a user to view the icons for the occupied beds color-coded based on the sex of the patient. In this view the screen, 172 may display the male occupied bed icons in blue and the icons for female occupied beds in pink. Flashing gray icons 178 may represent beds with pending discharges. Closed or inactive beds may be color-coded black as is the bed icon 180. Many other color-coded options are available via pull-down selector 179. These include patient and bed attributes such as gender, monitored bed, negative pressure room, and type of medical service (i.e. cardiology, surgery, orthopedics, etc.). In addition, each bed icon 178 can also display numeric values indicating how many hours remain until a patient is scheduled to be transferred or discharged. For example, the bed icon at 182 represents a patient having been requested to be transferred in 27 hours. The triangle at the lower right corner of the icon 182 indicates the receiving unit has not yet assigned a bed to the patient. Similarly, the patient in the bed represented by the icon 184 is scheduled to be discharged in 2 hours. Conversely, these numeric indicators can also indicate how long a patient has been in a given bed. This feature is important in that hospitals typically do not have an outpatient remain in a "outpatient status" for longer than 23 hours. The icon 186 has a triangle in the upper left corner used to identify the patient as an outpatient. The bed management system 10 can effectively alert (via flashing icons, audible alarms, e-mail, pager, phone call, etc.) the appropriate personnel when this 23 hour threshold has been reached or is near. Additionally, the negative numbers are used to indicate past due transactions. For example, if a patient is still occupying a bed 2 hours past a scheduled discharge, then the icon indicators would be –2D representing the overdue discharge.

Based on the role of the user, all bed assignment tasks, patient discharges, transfers, etc. can be performed from the floor plan screen 172 as well as the table view screen for a unit. Still referring to FIG. 19, the buttons at 188 provides a user access to various other screens including details of the patient or beds in the unit. Additionally, bed activity can be viewed at 190 for a selected bed. The buttons 192 and 194 provide a user access to additional screens and information as to pending transfers and discharges respectively. A user can select a particular bed in the floor plan view by clicking on the icon representing the bed. The icon 196 having a black border indicates a selected bed.

The unit floor plan screen 172 shown in FIG. 19 includes icons 198 to indicate the status of overflow beds. A legend indicator button 200 is provided to allow a user to display an onscreen floor plan legend indicating the attributes of the bed or patient identified by color-coded or other representations on the floor-plan view. Sample floor plan legends 202 are shown on screen 204 in FIG. 20 and in FIG. 21.

Figure 20:
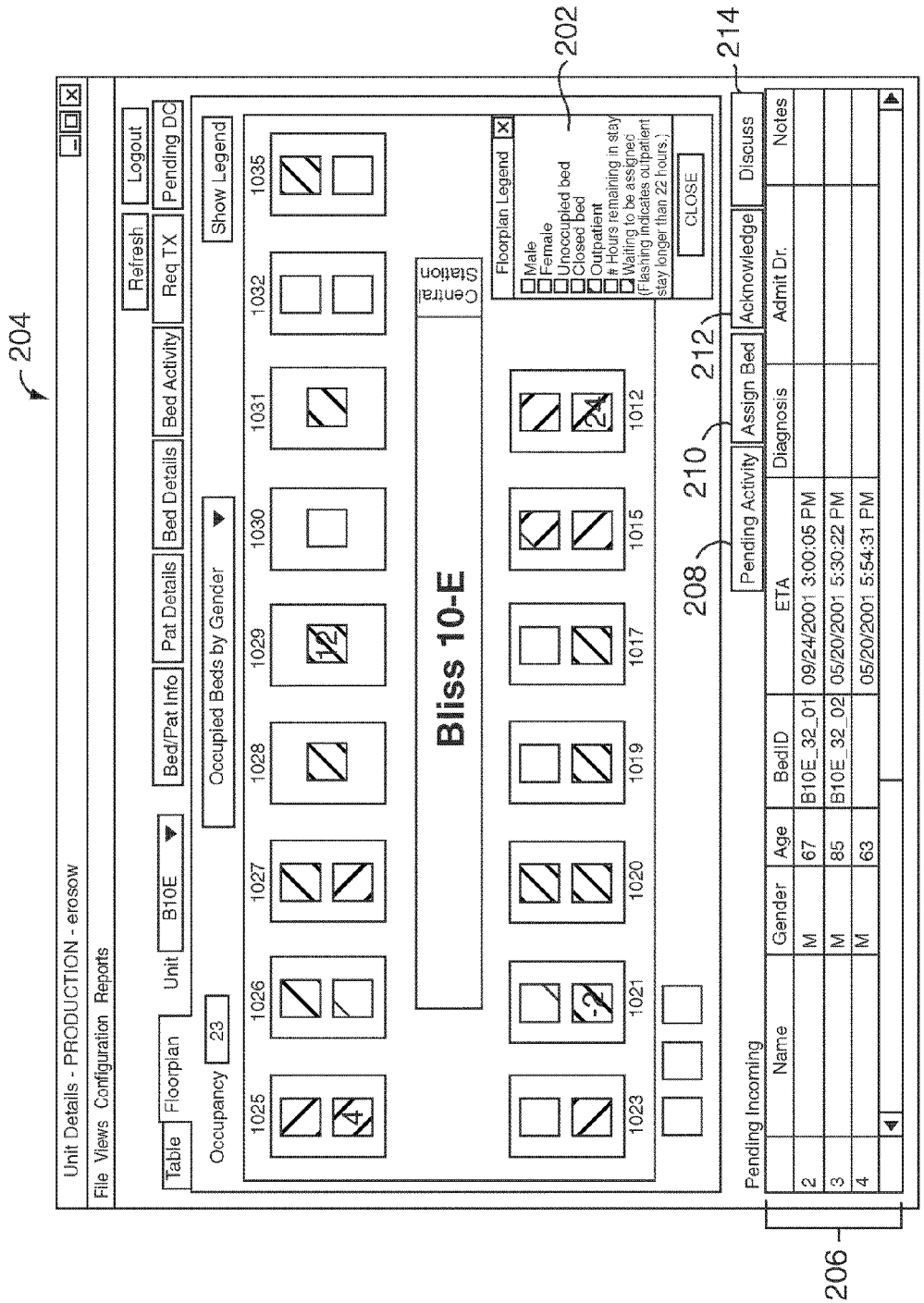
FIG. 20 is a user interface screen similar to the FIG. 19 embodiment including a pending incoming patient activity bar.
Figure 21:
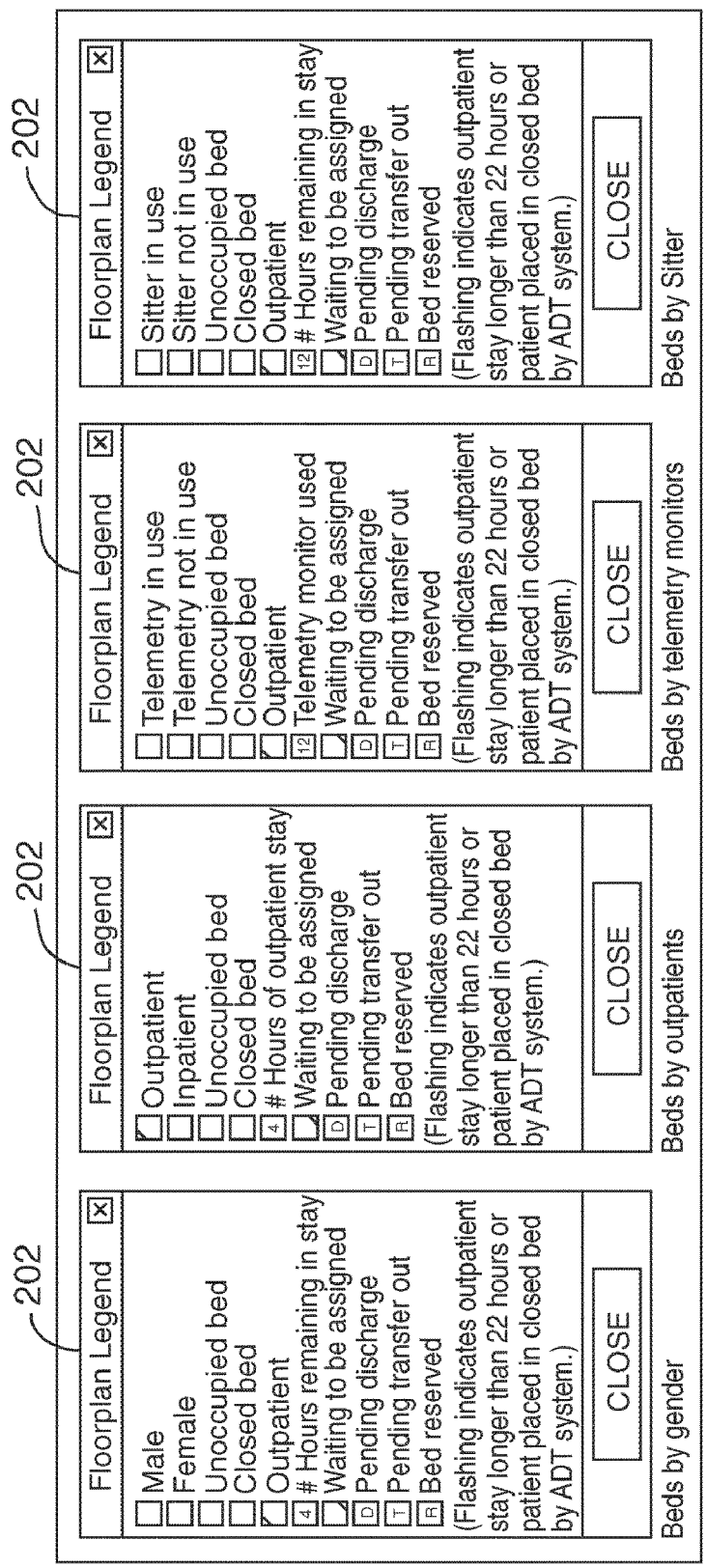
FIG. 21 is an illustration of legends for the unit detail floor plan views as used with the present invention.

Referring to FIG. 20, the bed management module 38 allows a user to view pending activities for the unit, in a lower portion 206 of the floor plan view screen 204. The pending activity button 208 allows a user to select various pending activities such as incoming patients, pending transfers, discharges, etc; as shown in screen 204, the selected activity is pending incoming, thus details related to pending incoming patients to the unit are displayed or accessible to the user. The assign bed button 210, can be used by a user to assign a selected patient a selected patient. Once the patient has been assigned a bed, the patient bed management module initiates requests to update the database 20 accordingly. In addition, the screen 204 will be updated wherein the patient's name will turn change in color from red to black indicating the patient has been assigned a bed and the selected bed will be reserved accordingly. The acknowledge and discuss buttons 212 and 214, respectively can be used by a user to acknowledge activities requested by other users or to contact or confer with other staff members regarding certain tasks or for other purposes. Once the incoming patient arrives on the unit, a user can update the patient's status in the system using the transfer or admit process of the system 10 and bed management module 38 depending on the patient's situation. The system 10 will updated the database 20 accordingly which will remove the patient from the pending incoming list and add the patient to an admitted list. Also the bed data will be updated to reflect the occupied status.

Figures 22, 23:
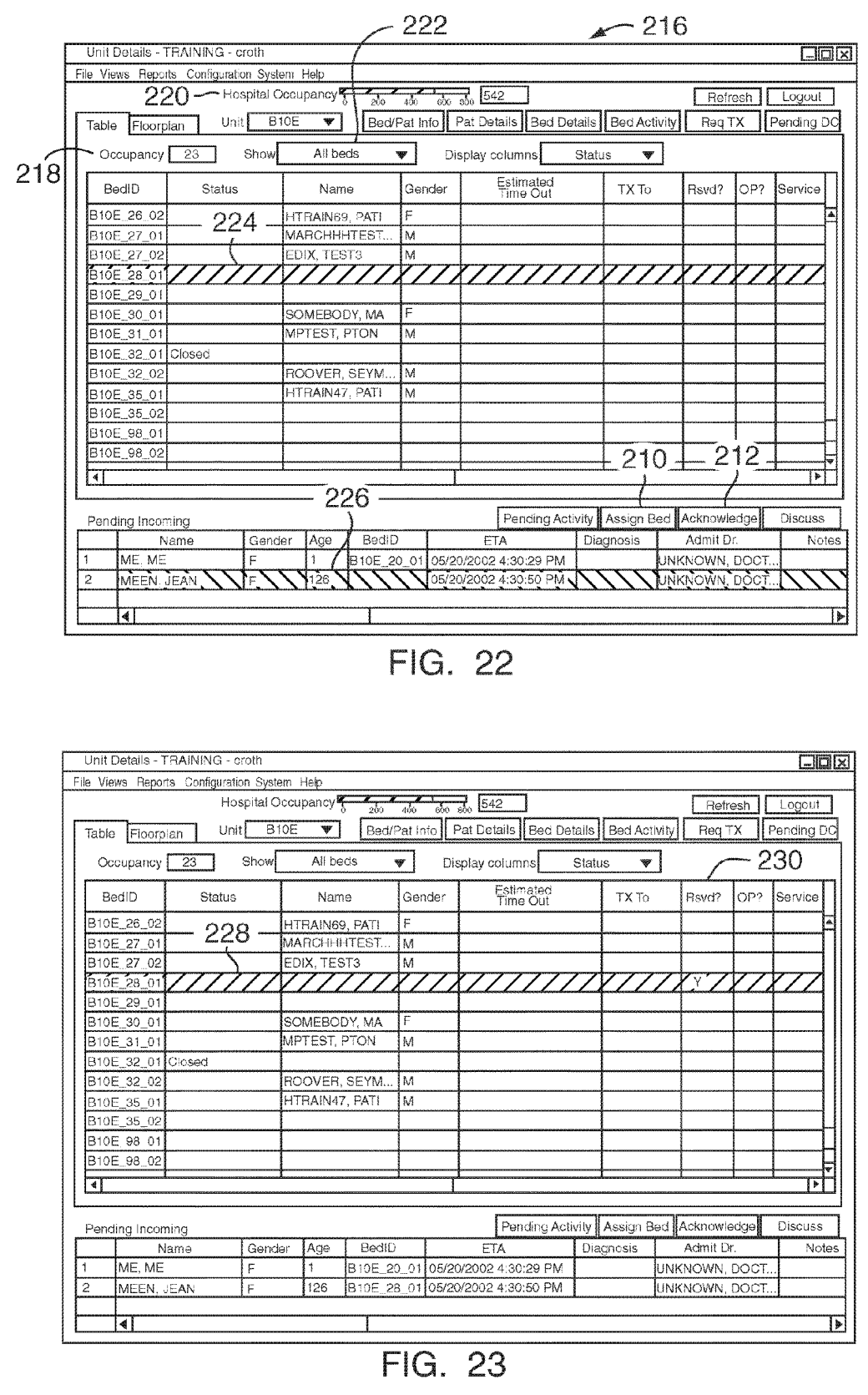

FIG. 22 illustrates a unit detail screen 216 in a table view. The screen 216 shows an occupancy level indicator 218 identifying the current occupancy of the unit and a hospital occupancy indicator 220 that the system 10 provides to allow the user to monitor the status of the health care facility. A bed attribute indicator 222 allows a user to view the beds in the unit select based on a selected attribute thereof. (for example, the indicator 222 shown allows the user to view all of the beds in the unit). The screen 216 shows a particular bed selected at 224 and an incoming patient selected at 226. As discussed above, a user can assign the selected patient to the selected bed using the assign bed button 210. FIG. 23 illustrates the unit detail screen 216 as updated, after the user assigns the patient 226 to the bed 224 as discussed above. The bed at 228 indicates a Y in the reserved column 230. The patient information at 226 has a bed ID number identifying the reserved bed.

Figure 24:
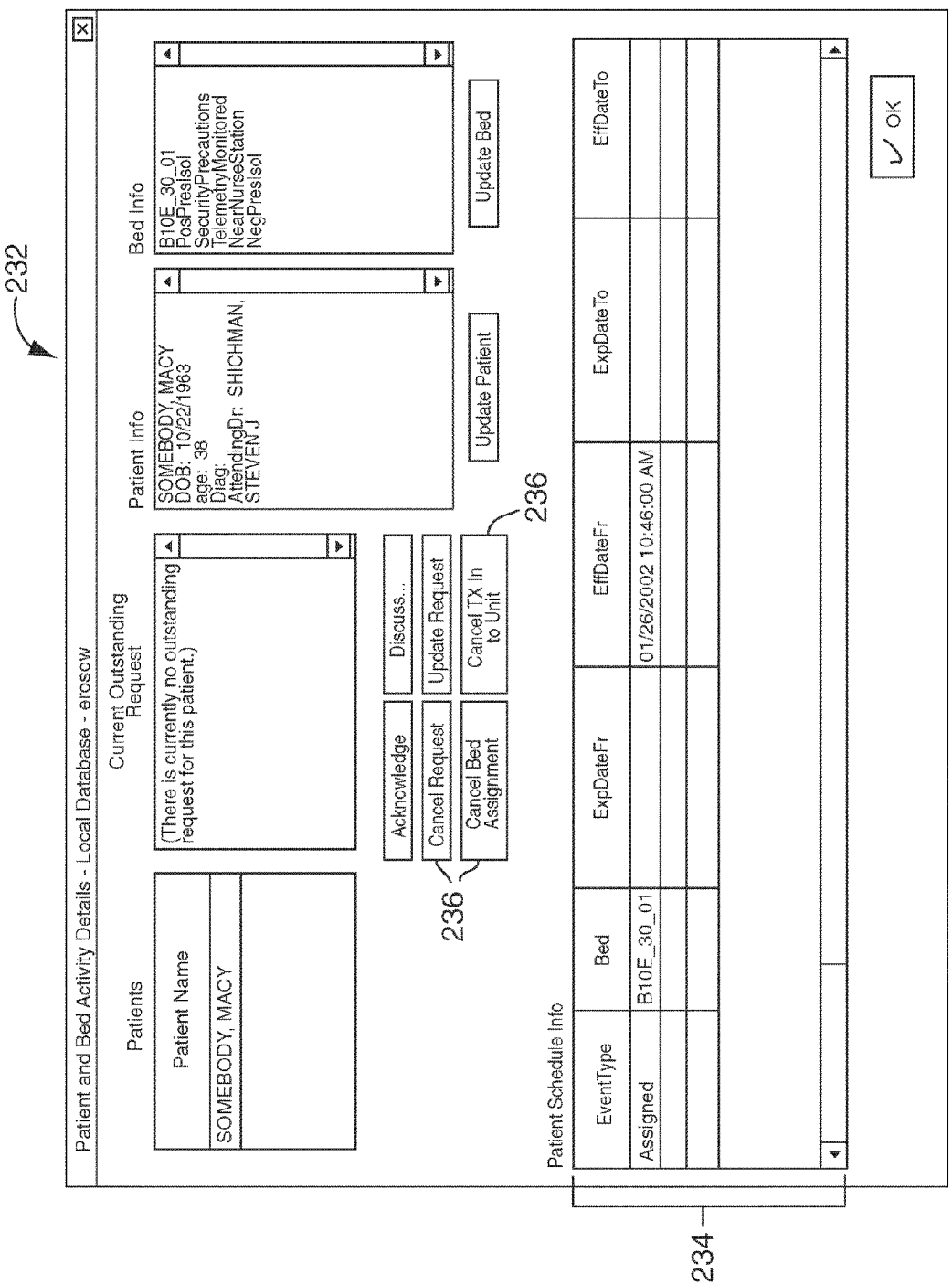
FIG. 24 is one embodiment of a user interface screen of the present invention bed management system showing patient and bed details for a selected patient as well as a patient schedule chart for the patient.

FIG. 24 illustrates one embodiment of a patient and bed activity user screen 232 provided by the bed management module 38 for providing a user to view, access and update detailed information related to the selected patient, the unit and bed. Additionally, a lower portion 234 of the screen 232 provides a user access to the patient schedule data for the selected patient. The patient schedule data is stored in the database 20 as shown in FIG. 6E. The user screen 232 includes cancel buttons 236 wherein cancel requests for a selected scheduled event or request can be initiated by an authorized user.

Figure 25:
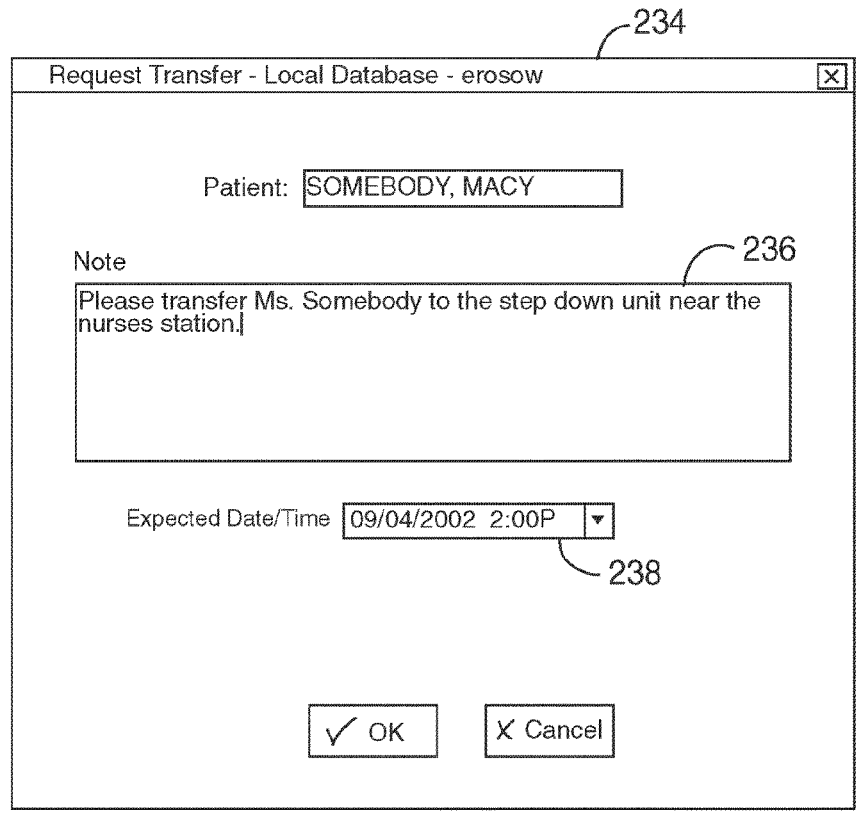
FIG. 25 is one embodiment of a user interface screen of the present invention bed management system for entering a transfer request for a patient.

FIG. 25 illustrates one embodiment of a request transfer user screen 234 that is accessible to a user by selecting a patient in a unit view and clicking the request transfer button shown referenced as 192 in FIG. 19. From the request transfer screen 234, the user can enter the details of a proposed patient transfer in the blocks 236 and 238. Upon clicking the OK button, a transfer request is initiated by the bed management module 38 including updating the patient schedule data and forwarding a message to the message handler 85 regarding the transfer request. In turn, the message handler will create appropriate messages to all appropriate recipients of the message including a user or role user at the receiving unit. The message handler 85 also transmits any necessary notifications required concerning the requested transfer. Upon acceptance of the transfer by a staff user at the receiving unit, the message handler 85 forwards a confirmation notice of the acceptance to the sending unit.

Figure 26:
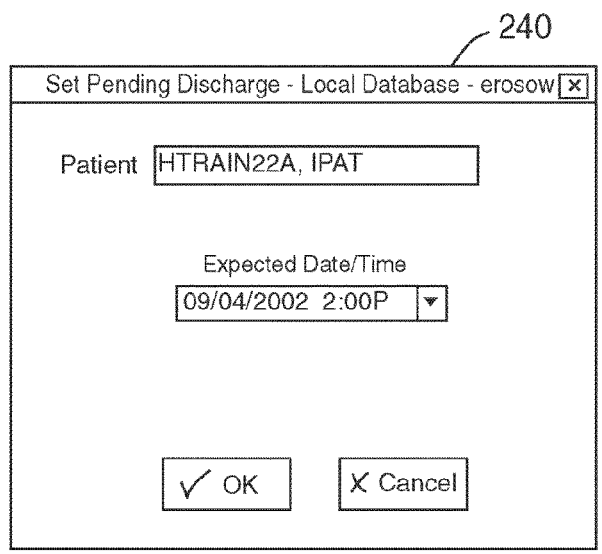
FIG. 26 is one embodiment of a user interface screen of the present invention bed management system for scheduling a discharge for a patient.

The bed management module 38 generates other user screens for handling various tasks associated with managing the bed assignments and bed occupancy of the health care facility. For example, FIG. 26 illustrates a user screen 240 generated by the system 10 wherein a user can schedule a patient discharge.

Figure 27:
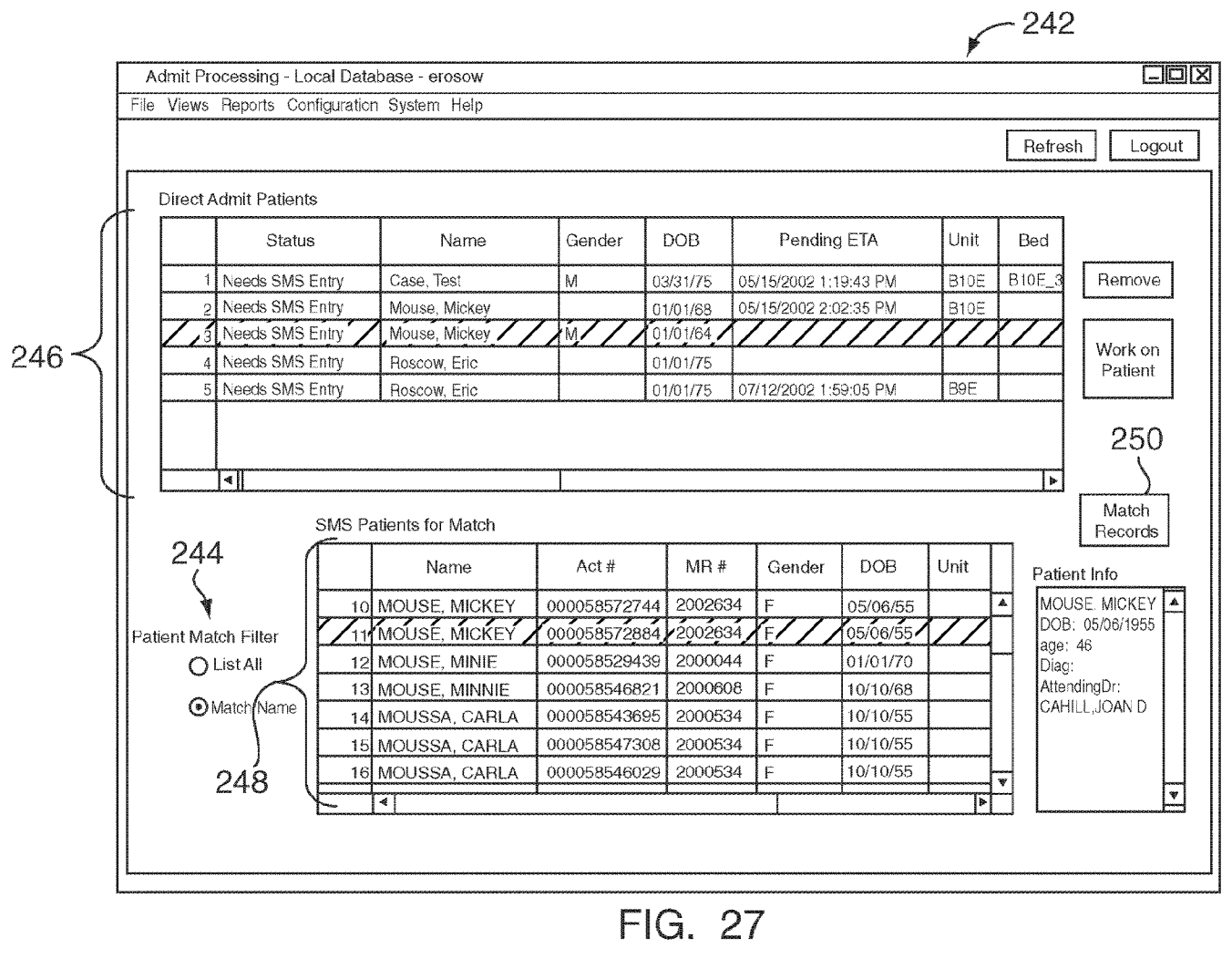

The database 20 can be merged with the ADT system to maintain accurate records in the bed management system 10. The bed management system 10 is designed to complement the network of the health care facility thus the merge function of the system 10 is not configured to update the ADT system 14, rather the database 20 is updated to match the records of the ADT system. FIG. 27 illustrates one embodiment of an admit processing screen for merging the records of the bed management system 10 with the appropriate record stored in the ADT system 14. The bed management system 10 can match an individual patient by name or provide a user with a list of all patients in the ADT system 14 upon user specification of the patient match filter indicator 244. A user can then select the correct patient record in each of the upper table listing of the patient records 246 of the bed management system 10 with the lower panel listing of the patient records 248 of the ADT system records. Clicking the match records button 250 merges the selected records wherein the bed management system 10 is updated to match the records of the ADT system.

Additionally, decisions for patient placement can be centralized or de-centralized. The bed management system 10 of the present invention provides for communication between all users of the system. The source and status of all decisions are automatically tracked and stored in the database 20. Additionally a monitoring process is capable of detecting and initiating notifications for any process delays. For example, Admitting or Emergency Departments can be automatically notified of bed placement decisions or delays thereof, if appropriate.

It should be readily recognized that the bed management system 10 of the present invention is capable of providing a variety of screens showing one or more additional features not previously discussed. For example, the bed management monitor 40 can generate upon request, pending activity charts showing both pending incoming and pending outgoing admissions, transfers and discharges for each unit, service group or for the entire facility. In the pending activity charts a user can define the scope of the displayed events in time increments. For example, the display will include only events that will occur in the next 3 hours, the next 12 hours, etc. Also, details of the origin of each request are accessible, such as information as to who made each request and when the request was initiated. In a preferred embodiment, a Pending Activity screen may be divided into upper and lower parts, where the top table shows the amount of pending activity coming in, and the bottom table shows the pending activity that is outgoing for a specified unit, service group, facility, etc.

The bed management system 10 can also interface with other ancillary information systems such as staffing or "time and attendance" systems and clinical information systems. This capability allows the system 10 to provide a wide array of multidimensional data such as: available (and required) staffing levels to meet occupancy demands, clinical information that may be useful in determining triage plans, etc.

Further, each of the user screens depicted in Figures include button features along the bottom of the screen for accessing features as printing, and navigating to various modules (i.e., Unit Details, Place Patient, Find Bed, etc.).

As will be apparent to one skilled in the art, the bed management system 10 assists the staff with everyday processes within the health care facility as well as provides summaries and analysis of the records for the entire facility or a portion thereof as well as the records of individual patients. The system 10 is configurable to provide efficient access to all parameters stored in the database 20 as well as summaries or analysis thereof. Administrators, program directors and the like, may view data over a wider scope that encompasses multiple units, services or physicians, for example. Longer-term, retrospective reporting is also supported, both by user-configured screen-based summaries, as well as by third party tools.

The server computer 12 of the bed management system 10 can also be interfaced to a health care facilities accounting system for generating reports in response to user queries regarding the budget and capacity of the facility. Alternatively, budget and financial data pertaining to the health care facility can be input and stored in the database 20 for use by the bed management system 10.

Figure 28:
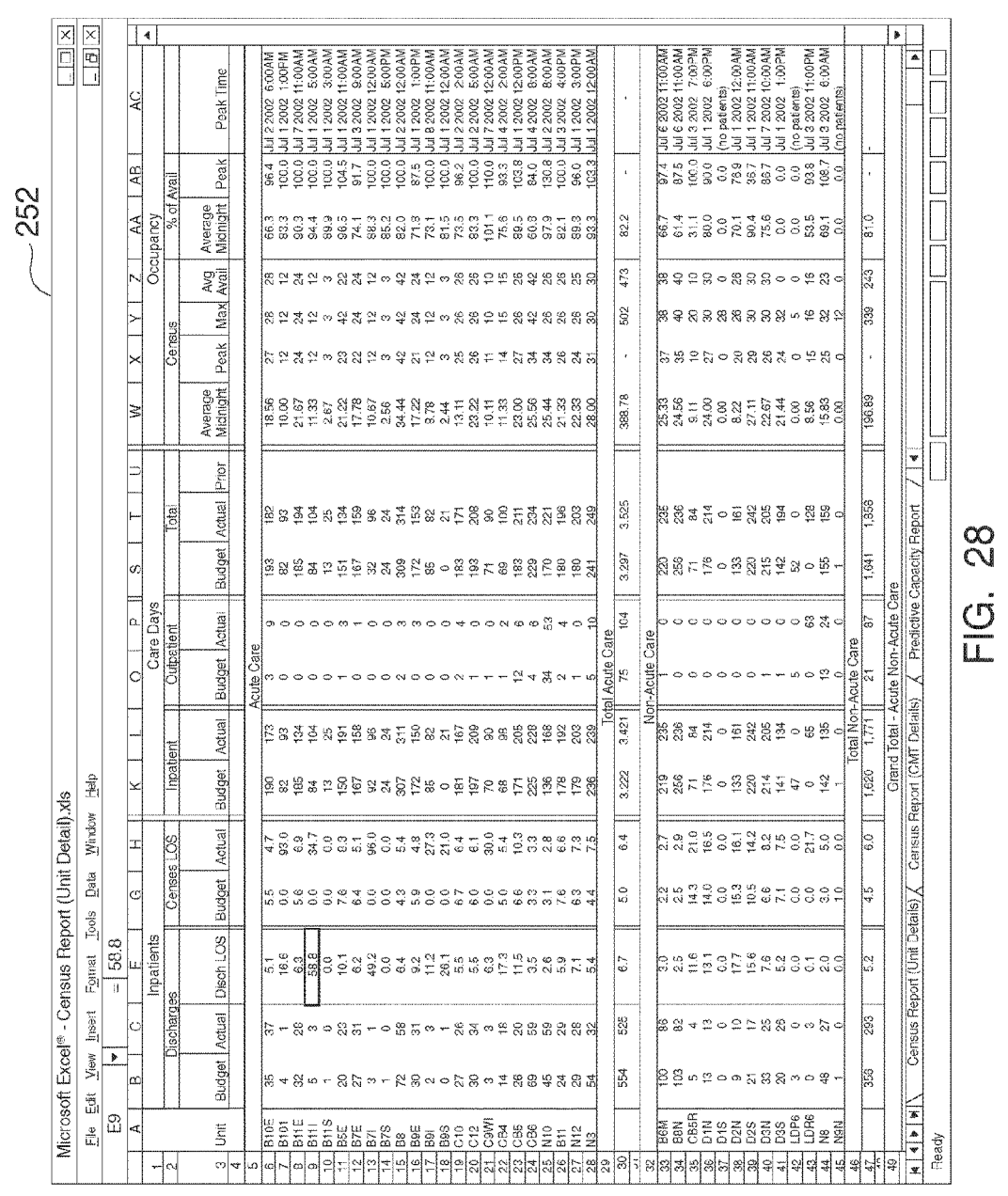

FIG. 28 shows an example of a census report 252 generated by the data mining and reporting module 40 that includes stratified census and budget details for the entire facility including summaries by unit, inpatient, out patient, acute units, non-acute units and service groups as well as budgeted discharge, length of stay and care day statistics. The report 252 also profiles average midnight census, peak census, including time and date thereof, maximum numbers of beds licensed for each unit as well as actual numbers of available beds for each unit. As mentioned above, a unit may have 40 beds licensed or available and staff for only 30 beds. Thus, the report 252 profiles the utilization of the entire health care facility. The data mining and reporting module 40 also generates comparative models for comparing the data of units or groups. Additionally, the bed management system 10 is configurable to provide summary reports similar to the census report 252 that profile and provide comparative models and reports for a plurality of health care facilities.

FIG. 29 shows an admissions coordinator (AC) report 254 generated by the data mining and reporting module 40 in response to a user request that profiles census information including bed occupancy and availability for a health care facility. To generate the report 254 a user selects a date and time for the data to be reviewed. Current and future reports can be generated. In the example report 254, each unit of a health care facility is listed by the service provided, the maximum number of beds, available beds, current occupancy, future (point in time, PIT) occupancy, resources, AM discharges (morning), male beds, female beds, mixed beds, private beds, non-committed beds, pending incoming and pending outgoing patients, monitored beds, negative pressure beds, positive pressure beds, comments, and added. This type of report 254 is useful for identifying available beds as well as managing bed capacity and occupancy levels of the health care facility. Additionally, a report such as the report 254, is useful to clear as many beds as possible if a large number of beds are needed on short notice such as in a major emergency. Many other data summaries and analysis reports can be generated by the data and reporting module 40 in response to user requests or automatically on a reoccurring basis for the use of the staff or administrators of the health care facility.

Figure 30:
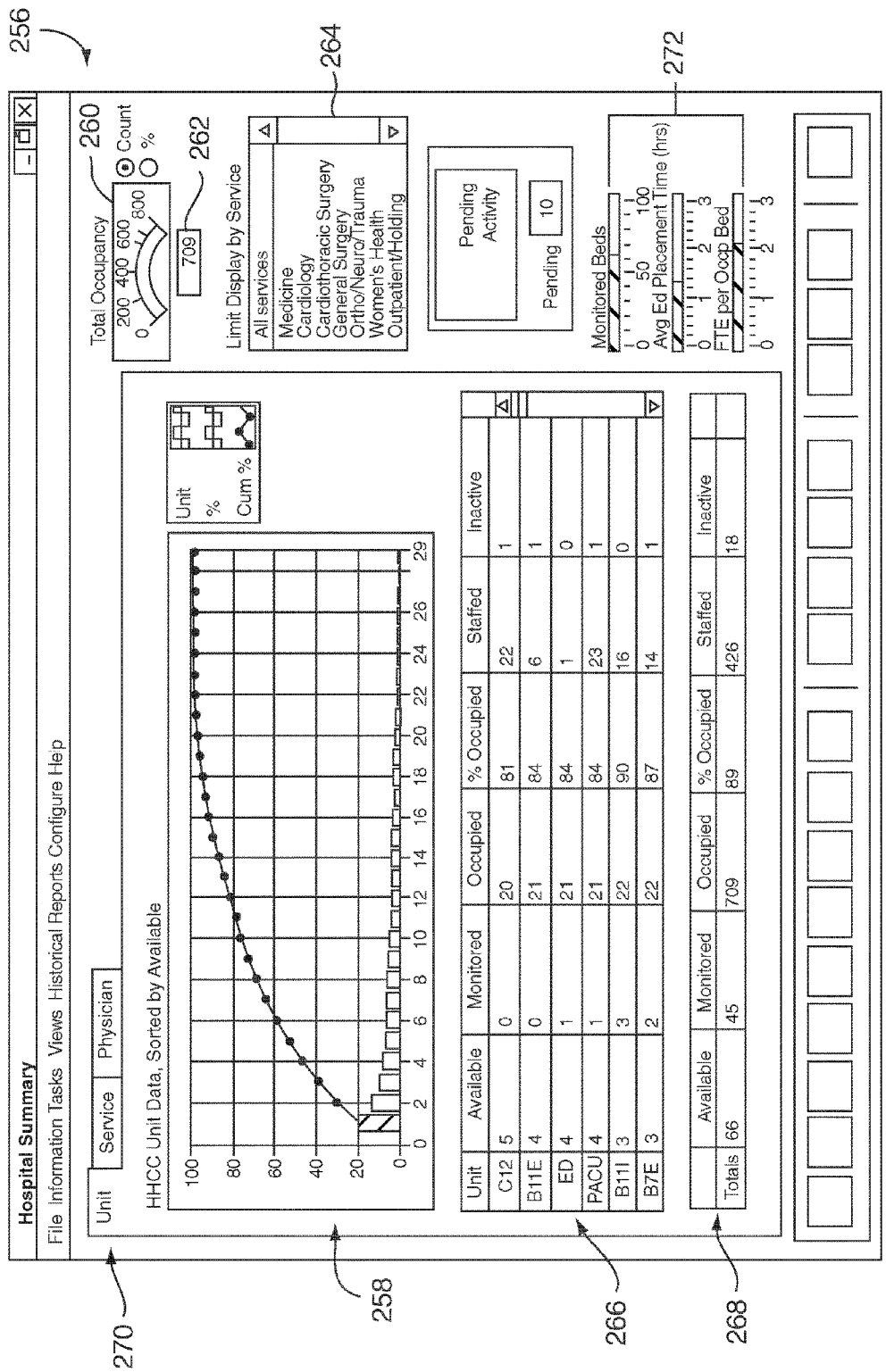
FIG. 30 is one embodiment of a hospital summary chart generated by the present invention for providing a summary of the status of a health care facility.

FIG. 30 shows an example of a hospital summary report 256 generated by the data mining and reporting module 40 of the system using Statistical Process Control (SPC) tools, including control and run charts, pareto analysis and multi-parameter analysis as well as other analysis tools. The data mining and reporting module 40 is particularly useful for monitoring and analyzing parameters in real time, such as patient occupancy and throughput, referral and payment patterns and network activity for the health care facility.

Referring again to FIG. 30, the hospital summary report 256 illustrates the use of table and pareto charts to profile various units and status summaries thereof. The chart 258 is includes both cumulative and pareto graphs showing the total occupancy for all units of a health care facility. A total occupancy indicator 260 identifies a current total occupancy count for the facility is 709 at block 262. A user can select a particular service group to profile at the limit display by service block 264. The report 256 presents a table display 266 of the current status of each unit of the health care facility. A table 268 shows totals for all of the units in the facility. The report 256 is an example only, in that the parameters displayed are variable and can be configured to display any available data stored in the database 20 as wells as functions thereof. For example, the patients could be aggregated by time of admission, length of stay, admitting diagnosis, etc.

Additionally, the patient statistics included in the report 256 can be displayed and analyzed by service or physician by using the indicator 270. Alternatively, the data summaries can be displayed using gauges 272. The gauges 272 in the report 256 display data such as monitored beds, average emergency department placement time, etc.

Figure 31:
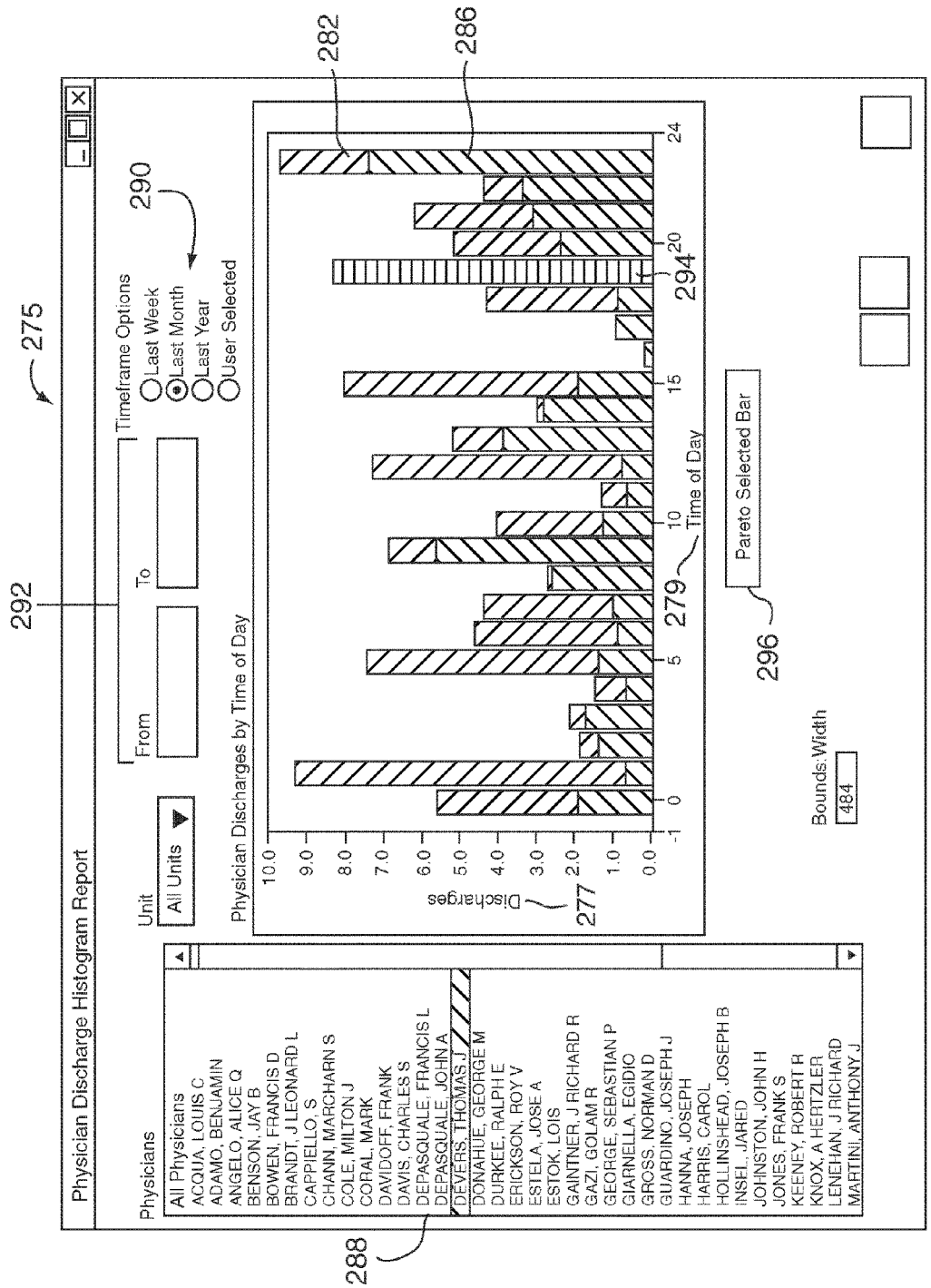
FIG. 31 is one embodiment of an interactive physician discharge histogram report generated by the present invention for summarizing the number of patient discharges as a function of time of day for a selected physician in comparison to all discharges.

FIG. 31 a physician discharge histogram report 275 generated by the data mining and reporting module 40. The report 275 shows a graph of the number of physician discharges 278 vs. the time of day 280. The total numbers for the all units of the facility are included in the dark bar graph 282, (all units selected using the pull-down indicator 284) vs. the discharges by a specified physician in the white graph 286 as selected in the physicians list at 288. The time frame for the graph is selected for one month using the indicator 290. Additionally, the time frame can be defined by the user by selecting user selected at the indicator 290 and entering a range of dates or dates and times at blocks 292. Also, details for the discharges for a particular time period, or bar of the chart, can be reviewed by selecting the particular bar in this case (1900 hour bar is selected at 294) and by clicking the pareto selected bar 296.

Figure 32:
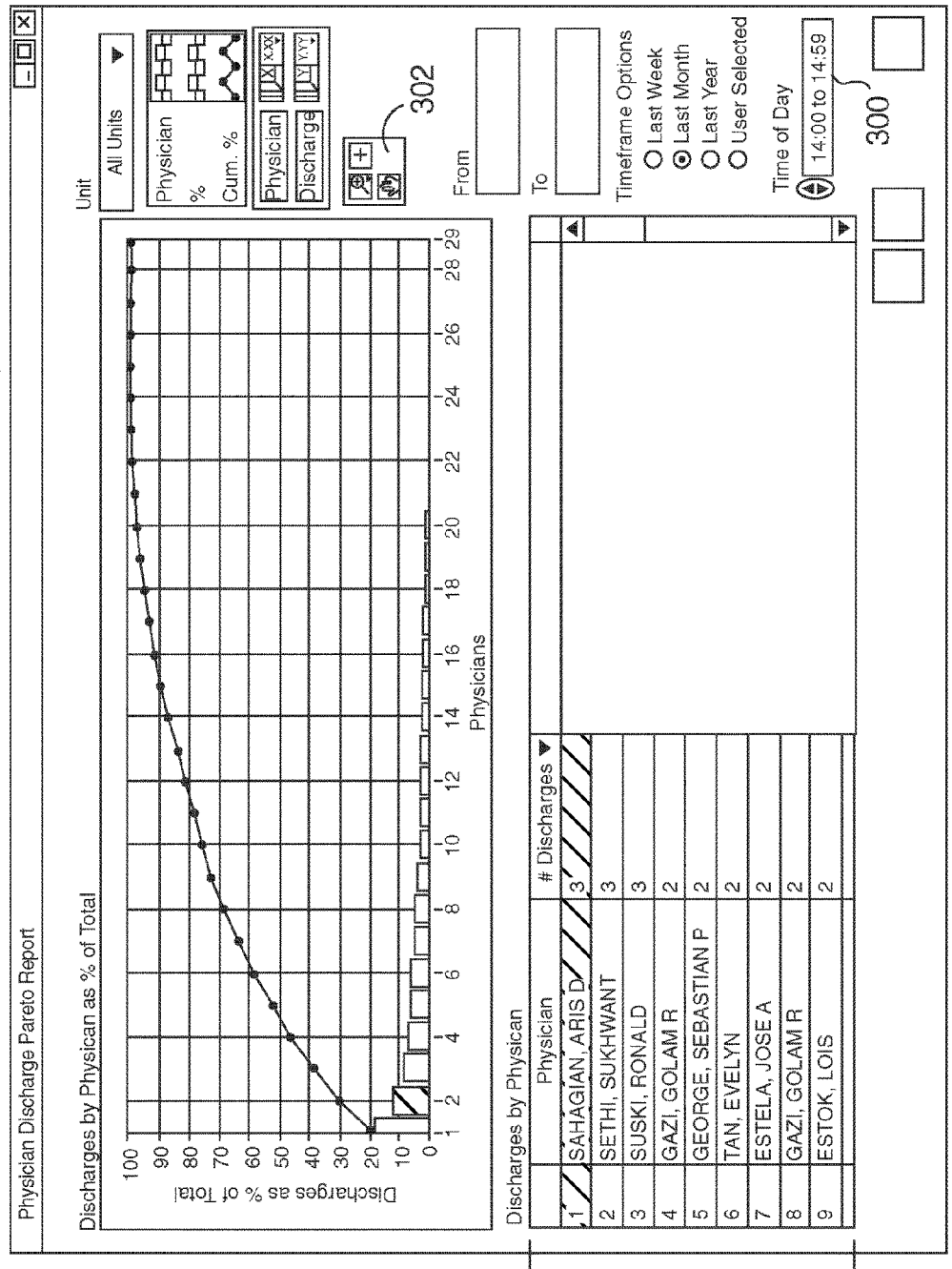
FIG. 32 is one embodiment of a detailed report showing the number of discharges for a selected physician during a selected time period as compared to all discharges for the facility; the report is user interactive wherein a user can specify variables to select a reconfiguration of the report.

FIG. 32 illustrates a physician discharge report 298 including a graphical representation showing all of the physicians and the number of patient discharges each had at the selected time period of 1900 hours as shown in the time of day indicator block 300. Zoom controls for the chart are shown at 302.

The number of discharges by each physician during the specified time range is included in the table 304.

FIG. 33 is an example of a compliance productivity report 306 generated by the data mining and reporting module 40 that graphically identifies the occurrence of specific events as a function of time in minutes. For example, the upper portion of the chart 308 shows the average time for all units (selected at 310) to complete a patient discharge during a specified time period at blocks 311 and 312. As shown in the chart 308, the average time to complete transport of a patient 313 is 20 minutes (for example, the time taken to transport the patient from the unit to the lobby), the discharge was documented at 314 and actually entered at 316. Also shown at 318 is the time average time for all units in the health care facility to submit a cleaning request, shown as 40 minutes, and the average time to complete cleaning of the room at 320 is 70 minutes. The report 306 can be used to improve turn-around time for the beds in a health care facility.

The lower portion of the report 306 is a histogram 322 of the selected event (in this case the average time to clean a bed for all units of the facility with +−3 standard deviations. FIG. 34 shows a detailed analysis of the average time to clean a bed by unit. The FIG. 34 graph 328 showing the average time for cleaning a bed by unit was generated by the data mining and report module 40 in response to a user selecting the average bar 324 shown in graph 322 of FIG. 33 and clicking the pareto selected bar 326. The table 330 shows the average time for cleaning a bed by unit for each unit of the facility during the time frames indicated. Further details for each unit and the staff thereof are accessible by selecting a particular unit.

The capabilities of the data mining and reporting module 40 through the use of analytical tools such as SPC and six sigma methodologies, as well as others allow the bed management system 10, to provide innumerable reports and analysis of the data stored in the database 20 as well as data exported from other applications and sources such as those mentioned above. For example, in the chart shown in FIG. 35, a trauma registry chart is shown wherein over 12,000 patients have been stratified and profiled into 252 unique diagnosis related groups (DRG). The chart in FIG. 35 details the top 20 most frequent DRG categories.

The SPC tools and other analytical tools are useful to visualize large data sets in a graphical form. The control chart shown in FIG. 35 is useful to view the variations of a process, using a series of rules and algorithms the SPC tools are used by the system 10 to distinguish between normal variation and special cause variations.

FIG. 37 illustrates another SPC chart that can generated by the data mining and reporting module 40 illustrating a real-time control chart having pre-established upper and lower control limits. An LED indicator turns red if a data element falls above or below the specified control limits. The lower left corner of the chart includes a range chart wherein a range of successive sample data points. The histogram in the upper right quadrant of the chart profiles the distribution of all data elements in real time. The data mining and reporting module can be configured to generate reports such as this for all of the stored data in the database 20 as well as functions thereof.

FIG. 38 shows a sample chart showing a tank simulation for a temperature valve, however this type of chart can also be generated for the health care facility data in the database 20 as suggested in the drawing. The heater could indicate directed resources from a bed manager or unit manager to appropriate units or service groups. The valve could be used to indicate if additional staff needs to be added to the health care facility.

The types of graphical reports and user interfaces identified above assist the staff and administrators of the health care facility to view and analyze information that may otherwise go unnoticed. The system 10 also notifies the users of any such situations as discussed herein. In addition, tools such as these help users plan for the future base d on historical and current events. Predictions can be made and assist to coordinate allocation of resources. For example, the histogram shown in FIG. 37 might be useful in determining peak occupancy or demand for the health care facility by time of day, day of week, week/month of the year, etc. This information can then be used to optimize access hours, staffing assignments and other resources related to the operation of the health care facility.

A key feature of the bed management system 10 of the present invention is its use of intelligent agents to provide assistance and alert the user of important alarm conditions that may otherwise go unnoticed. These agents can be configured to provide notification in the form of on-screen messages, using technology such as Microsoft's Merlin MSAgent 332 shown in FIG. 36, or via electronic notification (i.e. e-mails), pagers, facsimiles, synthesized voice phone messaging, and/or the like.

These online agents 332, as depicted in FIG. 36, are constantly monitoring and analyzing pre-configured or user defined patient, unit, facility, census information, etc. The agents 332 monitor and predefined conditions or situations, such as a high census in a unit (i.e. no available beds), excessive Emergency Department placement time for a particular patient, or delays in responses to placement requests.

The agents 332 can be configured to identify key indicators on reports or data stored in the database 20 related the health care facility or patients thereof, such as occupancy levels (number of available beds, number of monitored beds, etc. based on user defined thresholds and scope such as unit or facility limitations; outpatients who exceed 23 hour threshold in a bed; patients who have deviated from a critical path in which specific clinical protocols are applied to specific populations of patients, i.e. patients who have had a coronary bypass graft, CABG; patients who have underwent lateral transfers or have gotten bumped from one unit to another because of a more acutely ill patient needed the first patients bed; or patients who were admitted to non-ideal units due to lack of available beds in the ideal unit.

Other possible events or conditions that one or more agents 332 can be configured to monitor and report are such things as the average wait time in the emergency room wherein certain thresholds are predetermined; the activities of patients who have (or potentially have) communicable diseases and/or are immune suppressed (and therefore require either positive or negative pressure rooms); if the patient is a VIP; if the patient is being placed into a bed that is or will be occupied at the time of placement. Additionally, the agents 332 can monitor and report daily events such as admitting and discharge profiles by time of day, day of week, month of year, by physician, patient population, etc. These type of reports are especially important to hospitals because hospitals can make a major impact on their throughput and revenue collection if they can discharge more patients earlier in the day (i.e., before 11 am) instead of later in the afternoon.

Additionally, the intelligent agents 332 can be configured to provide alerts and notifications for innumerable conditions throughout the health care facility and the processes of the bed management system 10 related thereto such as:

alert for a bed manager or role user that a particular physician wants his patient to be on a specific unit and/or bed;

alert that a male patient is being placed into a female designated bed;

alert that that a patient suspected of having an airborne contagious disease (such as tuberculosis) is not being placed into a negative pressure room;

alert that a hospital census has surpassed 90, 95 or 100% of capacity or other threshold;

alert that a number of monitored beds (i.e., telemetry, hard wired) beds has surpassed 90, 95 or 100% of capacity or threshold;

alert that a number of available or staffed beds has surpassed 90, 95 or 100% of capacity or other threshold;

alerts as to the status of outpatients who have exceeded 23 hours in outpatient capacity;

alerts as to placement of a patient away from a nursing station who should be placed near a nursing station;

alerts of patient who might be a security risk (i.e., a gang member) placed near another patient that could increase the security risk (i.e., a rival gang member). Note that this security risk might not be created not only from the patients, but possibly also from their visitors;

alerts of attempted access to a user's account (security alert);

alerts if average wait time in the Emergency Room exceeds a specified limit (i.e., 2 hours);

alerts that a specific surgical procedure should be delayed or cancelled due to unavailable beds (for example);

alerts as to delays in patient transfers and/or discharges;

alerts as to unoccupied beds which due to housekeeping delays or mechanical problems;

alerts related to delays in bed turnaround times, such as that housekeeping delays that exceed targets (i.e., exceeded 20 minute target); and alerts on patient discharge entries that have been made more than 4 hours after the actual discharge occurred.

The above-identified list of possible conditions or data that can be monitored by configuring the intelligent agents 332 accordingly are possibilities for example only. The data mining and reporting module 40 can be configured to monitor any configuration of the data stored in the database 20 or reports or other analysis generated therefrom.

The above description and drawings are only illustrative of preferred embodiments which achieve the features and advantages of the present invention, and it is not intended that the present invention be limited thereto. By leveraging the power of current state-of-the-art software methodologies and open architecture standards, the bed management system of the present invention improves patient placement efficiency and saves time and money by assisting with the clinical and business decision processes associated with patient admissions, transfers and discharges. This integrated technology directly benefits health care providers, payers, and patients.

However, it is also envisioned that the bed management system of the present invention may be useful in applications other than a hospital environment, such as nursing homes, hotels, across multi-facility organizations as well by state or other agencies responsible for monitoring access (i.e. intensive care beds available statewide during a natural disaster) and the like.

The foregoing description of embodiments of the invention have been presented for the purpose of illustration and description, it is not intended to be exhaustive or to limit the invention to the form disclosed. Obvious modifications and variations are possible in light of the above disclosure. The embodiments described were chosen to best illustrate the principals of the invention and practical applications thereof to enable one of ordinary skill in the art to utilize the invention in various embodiments and with various modifications as suited to the particular use contemplated. It is intended that the scope of the invention be defined by the claims appended hereto.

What is claimed is:

1. A computer-implemented method for placing a patient in a location of a healthcare facility, comprising:
   (a) maintaining a database of a computer system, the computer system being configured such that the computer system communicates with a network, said maintaining comprising the steps of,
      (i) storing, in the database of the computer system,
         (A) patient attributes for a plurality of patients, and
         (B) bed attributes for a plurality of locations of the healthcare facility;
      (ii) continually monitoring a patient admissions/discharge system of the healthcare facility, and
      (iii) based on said monitoring, continually updating the data stored in the database of the computer system, the data stored in the database of the computer system being updated based on information from the patient admissions/discharge system contained in transactional messages, the information being automatically fed into the database; and
   (b) while maintaining the database in said step (a) by continually monitoring the patient admissions/discharge system and updating the data stored in the database,
      (i) receiving, by the computer system via the network from a client device configured to facilitate the provision of healthcare services, using a client server communication protocol, an identification of one of the plurality of patients whose patient attributes are stored in the database, the identification of one of the plurality of patients corresponding to a patient selected by a healthcare professional from a list of patients presented via a user interface provided by an end-user application for healthcare professionals loaded on the client device configured to facilitate the provision of healthcare services, and
      (ii) based on the patient identification received in step (b)(i), matching, by the computer system, requirements of the identified patient to available resources of the healthcare facility by comparing patient criteria of the identified patient with bed attributes stored in the database, the patient criteria comprising patient attributes for the identified patient that are stored in the database.

2. The method of claim 1, further comprising the step of assigning the identified patient to one of the locations of the healthcare facility that match the patient criteria in said step (b)(ii) by updating the data stored in the database.

3. The method of claim 2, wherein the assignment of the identified patient to one of the locations of the healthcare facility comprises assigning the identified patient to a specific bed of the healthcare facility.

4. The method of claim 2, wherein the assignment of the identified patient to one of the locations of the healthcare facility comprises assigning the identified patient to one of a plurality of units of the healthcare facility, each unit having a plurality of beds.

5. The method of claim 4, wherein the assignment represents a transfer of the patient.

6. The method of claim 4, further comprising the step of sending, to the client device using the client-server communication protocol, an identification of the location to which the patient is assigned.

7. The method of claim 1, wherein the patient criteria, by which the patient requirements are matched to available resources in said step (b)(ii), are specified based on the patient identification that is received in said step (b)(i).

8. The method of claim 1, further comprising the steps of,
   receiving, from the client device using the client-server communication protocol, patient information,
   searching the patient attributes stored in the database for a match between the received patient information and the patient attributes stored in the database, and
   sending, to the client device using the client-server communication protocol, an identification of those patients whose patient attributes match the patient information based on the search.

9. The method of claim 8, wherein the patient identification that is received in said step (b)(i) represents a patient selected from the identification of the patients sent based on the search.

10. The method of claim 8, wherein the patient information that is received and searched includes at least one of the group of patient name, patient date of birth, and patient identification number.

11. The method of claim 8, wherein the patient information that is received and searched includes at least one of the group of patient status, patient pre-admit day, patient pre-admit time, and patient medical service.

12. The method of claim 1, wherein the patient attributes that are maintained in the database include patient symptoms.

13. The method of claim 1, wherein the bed attributes include whether a bed is monitored.

14. The method of claim 1, wherein the bed attributes include an indication of medical services available at a bed.

15. The method of claim 1, wherein the bed attributes include an identification of pressurization of a room in which a bed is located.

16. The computer-implemented system of claim 1, wherein the bed attributes include an identification of gender of patients sharing a room in which a bed is located.

17. The method of claim 1, wherein the protocol is the Hypertext Transfer Protocol.

18. The method of claim 1, further comprising the step of receiving, from the client device using the client-server communication protocol, a request for placement of the identified patient in a selected location of the healthcare facility and, thereafter, assigning the patient to the selected location by updating the data stored in the database.

19. The method of claim 18, further comprising sending, to the client device using the client-server communication protocol, a confirmation of the assignment to the client computer.

20. The method of claim 1, further comprising a step of analyzing the data stored in the database to determine a proposed rearrangement of patient location assignments, by which a location is made available for the identified patient, if the searching in said step (b)(ii) results in no available location being identified for placement of the identified patient.

21. The method of claim 1, wherein the computer system comprises one or more computers.

* * * * *